US006915265B1

(12) United States Patent
Johnson

(10) Patent No.: US 6,915,265 B1
(45) Date of Patent: Jul. 5, 2005

(54) METHOD AND SYSTEM FOR CONSOLIDATING AND DISTRIBUTING INFORMATION

(75) Inventor: Janice Johnson, 2 Somerset La., Mill Valley, CA (US) 94941

(73) Assignee: Janice Johnson, Mill Valley, CA (US)

( * ) Notice: Subject to any disclaimer, the term of this patent is extended or adjusted under 35 U.S.C. 154(b) by 0 days.

(21) Appl. No.: 08/960,755

(22) Filed: Oct. 29, 1997

(51) Int. Cl.$^7$ .............................................. G06F 17/60
(52) U.S. Cl. ............................................... 705/2; 705/3
(58) Field of Search ......................... 600/300; 705/1–4, 705/40, 41; 380/22–24

(56) References Cited

U.S. PATENT DOCUMENTS

| | | | |
|---|---|---|---|
| 4,491,725 A | | 1/1985 | Pritchard ........................ 705/2 |
| 4,837,693 A | | 6/1989 | Schotz ........................... 705/4 |
| 5,072,383 A | | 12/1991 | Brimm et al. ................... 705/2 |
| 5,136,502 A | * | 8/1992 | Van Remortel et al. ........ 705/2 |
| 5,301,105 A | | 4/1994 | Cummings, Jr. ............... 705/2 |
| 5,307,262 A | * | 4/1994 | Ertel .............................. 705/2 |
| 5,359,509 A | | 10/1994 | Little et al. ..................... 705/2 |
| 5,471,382 A | | 11/1995 | Tallman et al. ............. 600/300 |
| 5,560,005 A | * | 9/1996 | Hoover et al. ................. 707/10 |
| 5,590,038 A | * | 12/1996 | Pitroda ......................... 705/41 |
| 5,659,741 A | | 8/1997 | Eberhardt .................... 707/104.1 |
| 5,704,044 A | * | 12/1997 | Tarter et al. .................... 705/4 |
| 5,737,539 A | * | 4/1998 | Edelson et al. ................. 705/3 |
| 5,748,907 A | * | 5/1998 | Crane ............................. 705/2 |
| 5,778,345 A | * | 7/1998 | McCartney .................... 705/2 |
| 5,867,821 A | * | 2/1999 | Ballantyne et al. ............. 705/2 |

FOREIGN PATENT DOCUMENTS

| | | |
|---|---|---|
| WO | WO 91/15817 | 10/1991 |
| WO | WO 95/03569 | 2/1995 |
| WO | WP 96/13790 | 5/1996 |

OTHER PUBLICATIONS

Perednia et al., Telemedicine technology and clinical applications, Feb. 1995, JAMA, vol. 273 No. 6, pp. 483–488.*

* cited by examiner

*Primary Examiner*—Joseph Thomas
*Assistant Examiner*—Christopher L Gilligan
(74) *Attorney, Agent, or Firm*—Glenn Patent Group; Michael A. Glenn

(57) ABSTRACT

A method and system are provided for consolidating and distributing information. Implementation of system functionalities for both restricted local and unrestricted system-wide uses are permitted. Open standards for hardware, software and firmware components and standardized medical codes, definitions and formats are supported. The preferred embodiment of the invention provides an integrated health care system. The invention can also be used to allow secure access to Social Security, annuity, retirement account, and benefit information, allowing individuals a unified view of their benefit and payment status. A centralized host maintains, consolidates, and redistributes information generated at all networked locations. Information is electronically transferred among the system components to link an individual's local records to those stored remotely. The individual information device, centralized host computer, and any other computers or networks linked to the system can therefore be automatically updated. An individual information device stores a service recipient's insurance information, a emergency records and critical health care histories. This information is accessed by the system for use in managing any aspect of the service recipient's health care. Portable terminals can be used to access the system. A portable terminal can also be used independently from the system to perform health care functions. Unrestricted system-wide, or restricted local uses are supported. Insurance coverage for services and treatments can be determined and the information transmitted directly from the carrier(s) to the service recipient and service provider(s). Supported features include service authorization, messaging, diagnostic services, coverage determination, billing, and electronic payment.

22 Claims, 9 Drawing Sheets

METHOD AND SYSTEM FOR CONSOLIDATING AND DISTRIBUTING INFORMATION

BACKGROUND OF THE INVENTION

1. Technical Field

The invention relates to information processing. More particularly, the invention relates to a method and system for consolidating and distributing health care records.

2. Description of the Prior Art

Providing effective management and organization for the health care system is a continuing need. Many attempts have been made to improve communication, for example, among insurers, health care providers, health plan sponsors, and patients. However, the health care system is still subject to significant problems in accurate record maintenance, access to information, and communication among various organizations and agencies.

Pritchard, Medical Insurance Verification and Processing System, U.S. Pat. No. 4,491,725 (1 Jan. 1985) discloses a system for verifying and determining a patient's background medical and insurance coverage. However, Pritchard does not integrate other essential participants in the modern health care system. For example, a user cannot locate and schedule appointments with health care specialists, or research treatment options using the system disclosed in Pritchard.

Each user of an integrated health care system may maintain records and computer operations that are not to be distributed to the other users of the system. Such information as personnel records and internal disciplinary records are typically confidential. However, it can be desirable for the user to also be able to access these records as a part of the integrated health care system. For example, the user may wish to compare the treatment requirements of a patient with the discipline records of a health care practitioner to determine if it is appropriate to assign a case to a particular practitioner. It is therefore desirable that the integrated health care system permit both restricted local and unrestricted system-wide uses. However, the Pritchard system does not disclose the structure or functionalities for providing both such local and system-wide uses in the same system.

Cummings, All Care Health Management System, U.S. Pat. No. 5,301,105 (5 Apr. 1994), describes a system for integrating the participants in a health care system. The Cummings system is designed for use by those directly involved in an individual patient's health care program. Such users include the patient, health care provider, bank or other financial institution, insurance company, utilization reviewer and employer. However, the Cummings system is not designed for use by other participants in the health care system, such as medical researchers, and public agencies. Furthermore, Cummings does not disclose support for health care data reporting standards. Thus, the various users of the Cummings system will need to convert the non-standardized information retrieved from the system for use in other health care reporting applications.

Additionally, Cummings does not support auxiliary functionalities that are often essential to providing total health care for a patient. For example, Cummings does not disclose support for such functionalities as Social Security, annuity, retirement account, and other benefit information.

The rapid transmission of data to the appropriate sources is frequently of critical importance in providing health care. Portable input devices, such as personal digital assistants, are increasingly being used for creating, maintaining, and transmitting data records. However, neither Cummings nor Pritchard discusses the use of such portable input devices.

It would therefore be an advantage to provide a method and system for integrating the various participants in a health care system that permits both restricted local and unrestricted system-wide uses. It would be a further advantage if such method and system supported auxiliary functionalities related to providing total health care. It would be yet another advantage if the method and system supported the use of portable data input devices to rapidly create, maintain, and transmit data records.

SUMMARY OF THE INVENTION

The invention provides a method and system for consolidating and distributing information. Flexible configuration and access options provide an array of options to best meet the needs of the service provider's personal workstyle and required volume of information. The system permits implementation of system functionalities for both restricted local and unrestricted system-wide uses. Open standards for hardware, software and firmware components and standardized medical codes, definitions and formats are supported.

The preferred embodiment of the invention provides an integrated health care system, managing all facets of modern health care, including individual service recipient care, public health, and health care policy. The invention is used to consolidate health care records, for example for diagnostic and research purposes, and to permit immediate access to time critical health care information. However, alternative embodiments of the invention can be used to capture, store, and process other types of information. For example, the invention can also be used to allow secure access to Social Security, annuity, retirement account, and benefit information, allowing individuals a unified view of their benefit and payment status.

The invention provides centralized record collection and facilitates the transfer of information among the different system components by electronically linking an individual's local records to those stored remotely, such as on the computer systems of insurance companies, health care service providers, health plan sponsors, medical researchers, and service support. A complete record of individual care is thereby provided.

Such links between the individual service recipient's records and other information systems permit the immediate transfer of results and information among specialist service providers and sites, libraries of scientific literature and bibliographic information, institutional databases and registries, researchers, and records of family members. Insurance coverage for services and treatments can be determined and the information transmitted directly from the carrier(s) to the service recipient and service provider(s).

In the system, an individual service recipient is provided an individual information device that stores the service recipient's insurance information, as well as emergency records and critical health care histories. In the preferred embodiment, this individual information device is an integrated circuit (Smart) card. However, the information device may include any appropriate means for storing and/or encoding information, such as magnetic storage cards or any other types of portable integrated circuit or microchip-based devices.

A service provider accesses the information on the individual information device, for example, by swiping the card through a card reader linked to a remote terminal or to a single or networked provider terminal. Such terminals include portable computers and personal information devices, or any desktop computer or networked computer.

In one embodiment of the invention, the invention is implemented using a local area network (LAN) or intranet. In this embodiment, information is transmitted from, for example, the portable personal device, to the LAN or intranet Server. This information may then be accessed by any workstations on the internal network and can be transmitted from the LAN or intranet Server to the host computer.

In the preferred embodiment of the invention, the terminal is a portable device. This portable device can optionally be used to communicate with the entire system, any portion of the system, or independently from the system. Restricted local and unrestricted system-wide uses can therefore be implemented.

A centralized host processing system is used to maintain, consolidate and redistribute information generated at all access endpoints, such as from the individual information device, with stored information and from any computer or other processing and storage device on the centralized network. The centralized host processing system can be, for example, a computer network, or a plurality of such linked networks having a central server. The consolidated information is then distributed to various locations on the network, for example, in response to a query.

Service information, formatted service recipient records, and potential diagnostic codes are transmitted across the network between the remote or provider terminal and the host computer(s). The individual information device, centralized host computer, and any other computers or networks linked to the system can therefore be automatically updated.

Services can be authorized through access to the central host(s), which can also calculate the costs of the services, as well as the amount of available insurance coverage. The invention can be used to generate billing information and to electronically transfer funds from sources such as insurance carriers, bank accounts, and credit card accounts.

Each Insurance carrier can be electronically billed for the amount charged to that carrier. The Insurance carrier can then pay the bill by electronically transferring funds to the service provider's account at a specified payment interval. Payment histories can be also be electronically transferred from the Insurance carrier to the service provider on the network. The charges to the service recipient can also be calculated and transmitted to the service recipient.

In the preferred embodiment of the invention, an on-line diagnostic service is provided, such as a software application or an on-line diagnostician. Additionally, the system can be integrated with statistical analysis software packages, for example, to monitor patterns in national health care, or to plot the distribution of cases of an infectious disease.

The invention supports messaging and scheduling services, including electronic mail (e-mail), voice mail, and paging. Appointment records and administrative information can also be distributed through the system.

Service historical records stored on the system can be accessed by researchers for full data analysis. The invention supports research requests for analysis of any of the elements of the system, such as for analyzing legal compliance or disease management. Such historical records can be stripped of identifying information before being distributed to researchers.

The invention promotes marketing and enrollment efforts for new and current plans. Changes, for example, in plan memberships, benefits, personal information, or health care information can be automatically transmitted to the various participants in the system.

The invention permits participants to search records for health care providers and organizations. Such records can include licensing information, staffing affiliations, organizational ownership information, tax identification information, curriculum vitae of licensed practitioners, as well as information regarding disciplinary actions. Service recipients can access and review the contents of their health care record and perform searches of research databases, for example, regarding treatment options, and toward development of a care contact network.

DETAILED DESCRIPTION OF THE INVENTION

Figure 1:
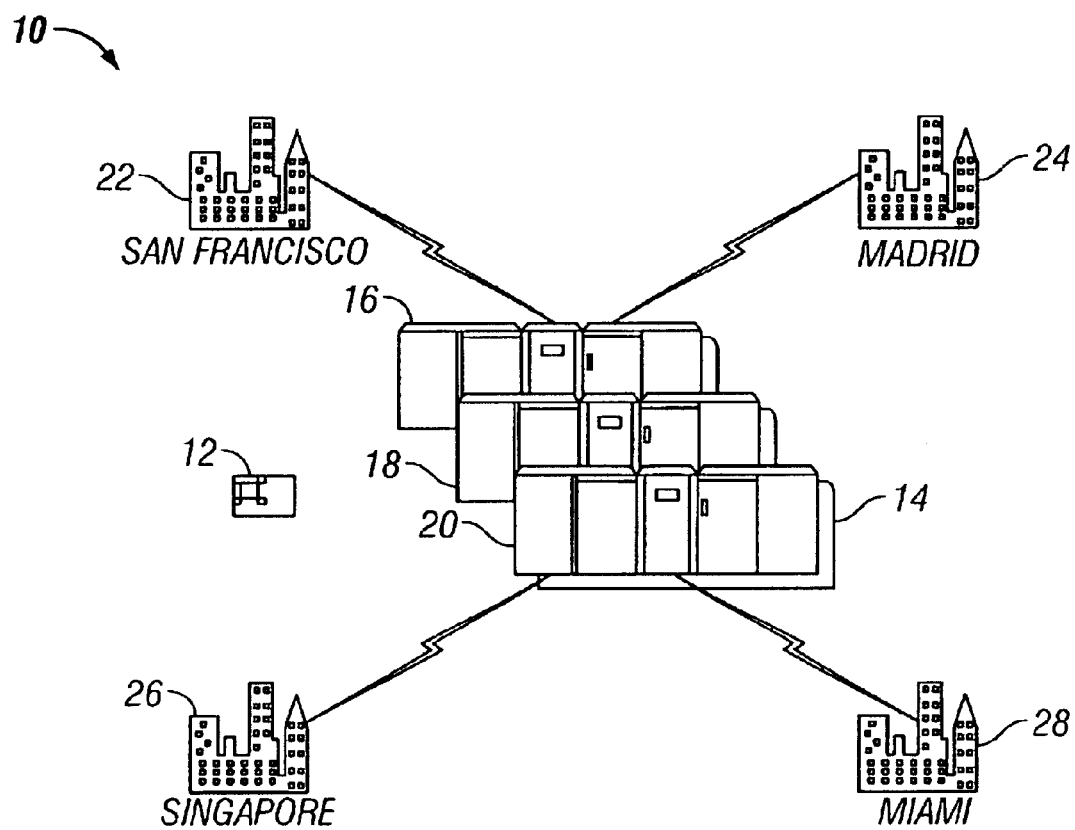
FIG. 1 is a diagram of the system for consolidating and distributing information, according to the invention.

The invention provides a method and system for consolidating and distributing information. Flexible configuration and access options provide an array of options to best meet the needs of the service provider's personal workstyle and required volume of information. The system permits implementation of system functionalities for both restricted local and unrestricted system-wide uses. Open standards for hardware, software and firmware components and standardized medical codes, definitions and formats are supported.

The invention creates an infrastructure for health care and benefits management resulting in:

(1) support of service recipient care and improvement of quality;
(2) enhancement of the productivity of health care professionals and reduction of administrative costs associated with health care delivery and financing;
(3) support of clinical and health services research;
(4) accommodation of future developments in health care technology, policy, management and finance; and
(5) ensuring service recipient data confidentiality.

The preferred embodiment of the invention provides an integrated health care system, managing all facets of modern health care, including individual service recipient care, public health, and health care policy. The invention is used to consolidate health care records, for example for diagnostic and research purposes, and to permit immediate access to time critical health care information. However, alternative embodiments of the invention can be used to capture, store, and process other types of information. For example, the invention can also be used to allow secure access to Social Security, annuity, retirement account, and benefit information, allowing individuals a unified view of their benefit and payment status.

The invention provides centralized record collection and facilitates the transfer of information among the different system components by electronically linking an individual's local records to those stored remotely, such as on the computer systems of insurance companies, health care service providers, health plan sponsors, medical researchers, and service support. A complete record of individual care is thereby provided.

Such links between the individual service recipient's records and other information systems permit the immediate transfer of results and information among specialist service providers and sites, libraries of scientific literature and bibliographic information, institutional databases and registries, researchers, and records of family members. Insurance coverage for services and treatments can be determined and the information transmitted directly from the carrier(s) to the service recipient and service provider(s).

Services can be authorized through access to the central host(s), which can also calculate the costs of the services, as well as the amount of available insurance coverage. The invention can be used to generate billing information and to electronically transfer funds from sources such as insurance carriers, bank accounts, and credit card accounts.

Links may also be provided to decision support systems, such as diagnosticians, thereby increasing the treatment information available to service providers. Additionally, the system may be integrated with statistical analysis software packages, for example, to monitor patterns in national health care, or to plot the distribution of cases of an infectious disease.

The invention therefore provides the data and processes necessary to improve current and future health care services and promote disease management, while reducing administrative costs and simplifying payment processing for health care providers and health care customers.

In this application, the term "function" refers to a business related procedure that can be performed in one or more steps, or "processes". These steps can be manual, automated, or both. Processes often cross departmental and organizational boundaries. Re-design or re-engineering such processes can often improve management operation and functions, resulting in significant time and cost savings. Components are subsets of a functional process. Additionally, in this application, "user groups" are the users of certain system functions.

FIG. 1 is a diagram of the system for consolidating and distributing information, according to the invention. In the system 10, a participating individual is provided with an individual information device 12. In the preferred embodiment, this individual information device is an integrated circuit (Smart) card. However, the information device may include any appropriate means for storing and/or encoding information, such as magnetic storage cards or any other types of portable integrated circuit or microchip-based devices.

A centralized host processing system 14 is used to maintain, consolidate and redistribute information generated at all access endpoints, such as from the individual information device (not shown), with stored information and from any computer 16, 18 or other processing and storage device on the centralized network. The centralized host processing system can be, for example, a computer network, or a plurality of such linked networks having a central server. The consolidated information is then distributed to various locations 22, 24, 26, 28 on the network, for example, in response to a query.

Figure 2:
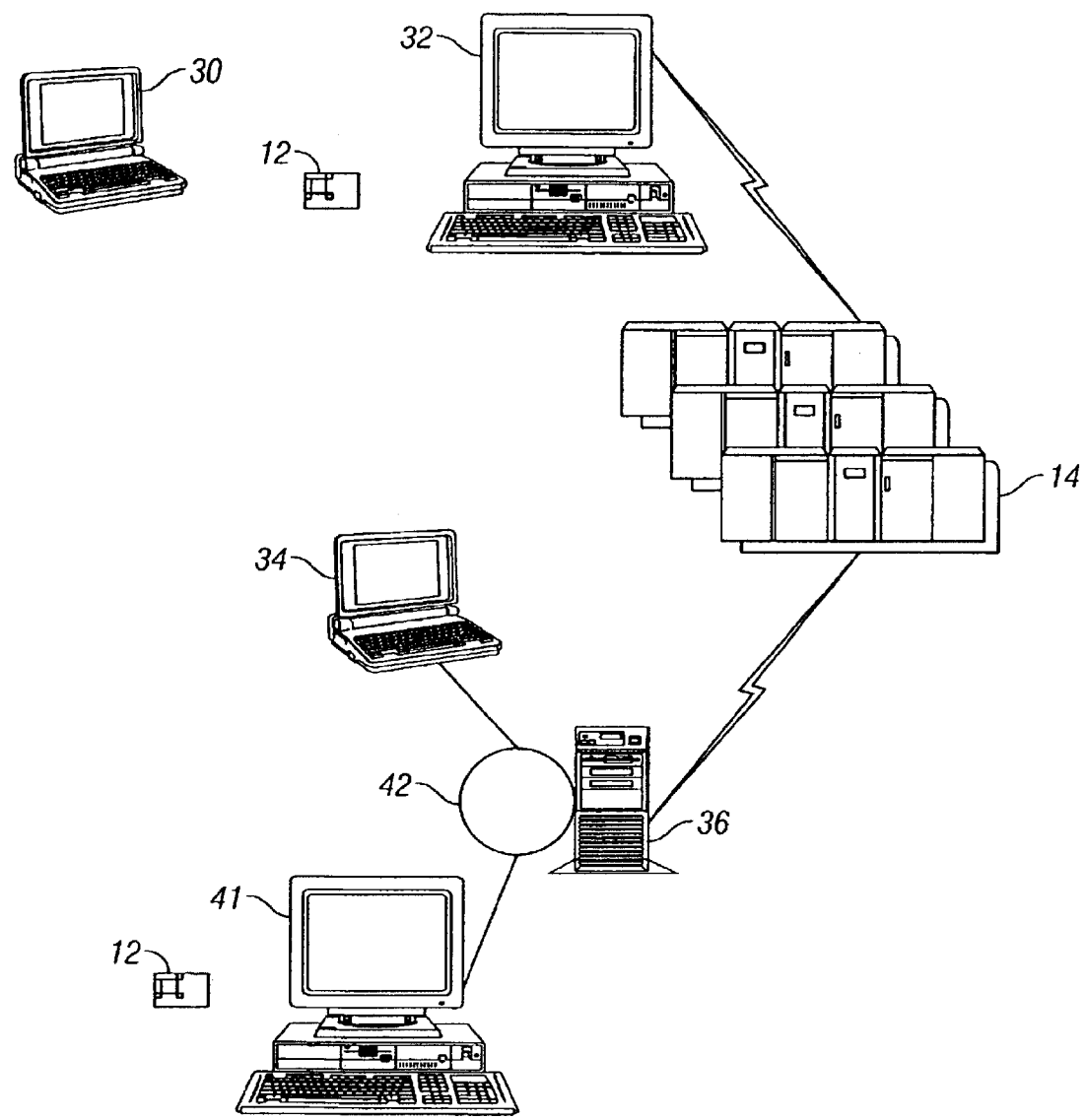
FIG. 2 is a diagram of the components of the system for consolidating and distributing information, according to the invention.

FIG. 2 is a diagram of the components of the system for consolidating and distributing information, according to a preferred embodiment of the invention. An individual is given an individual information device 12 that stores the individual's insurance information, as well as emergency records and critical health care histories. This information may be encrypted.

A service provider accesses the information on the individual information device, for example, of a health care service recipient. When the individual information device is a smart card, the information is accessed by swiping the card through a card reader linked to a remote terminal 30 or a single or networked provider terminal. Such remote terminals include portable computers and personal information devices and provider terminals can include any computing device operating in either a stand-alone mode or connected to other computing devices through a local area network, intranet, wide area network or any other interconnected mode.

In the preferred embodiment of the invention, the terminal is a portable device. This portable device can be optionally be used to communicate with the entire system, any portion of the system, or independently from the system. For example, a personal digital assistant can be used by a physician to access a patient's medical records stored on a central host. The personal digital assistant can also be used on access confidential information stored in a database that is not connected to the network, such as files stored in the physicians personal computer. In addition, the personal digital assistant can be used independently from the system, such as to maintain work and appointment schedules, or to store personal notes.

Service recipient information is transmitted from the remote terminal or provider terminal across the network to the host computer(s) 14. Information such as detailed histories and records stored on the host computer are accessed and downloaded to the service provider's computing device 32 or to a high volume configuration such as a localized server or host 36. The individual information device may then be updated by new information in the information downloaded from the host computer 14.

Formatted service recipient record and potential diagnostic codes may be downloaded from a network server, or the host computer to a portable personal device or terminal for use by a health care practitioner, for example, during an appointment with the service recipient. Information gathered by the practitioner may also be uploaded to the server, host computer, or individual information device. Thus, for example, the service recipient will be provided with an updated electronic record of new procedures and medications prescribed by the health care practitioner and the service recipient information on the central host computer will also be updated to reflect the changes. Appointment records and administrative information may also be distributed through the system. Thus, a health care practitioner may view the day's scheduled appointments, receive health care records for each service recipient, record relevant information from each appointment, and receive memos from, for example, an insurance carrier or a hospital using the portable personal device or provider terminal. In one embodiment of the invention, the invention is implemented using a local area network (LAN) or intranet 42. In this embodiment, information is transmitted from, for example, the portable personal device 12, to a computer 34 that is connected to the LAN or intranet server 36. This information may then be accessed by any workstations or other computers 41 on the internal network and can be transmitted from the LAN or intranet server to the host computer 14.

In the preferred embodiment of the invention, an on-line diagnostic service is provided. In one embodiment, this service is a software application. This application allows a service provider or service recipient to identify symptoms and search for potential diagnoses, procedures, medications or pharmaceuticals, support groups, specialists and other care options, pertinent research, on-line video, audio and other multimedia options. The software application also provides communication access features to individuals and organizations.

In an alternative embodiment, the diagnostic service is an on-line diagnostician. For example, the practitioner can submit information and questions through the network to an on-call physician. The physician can then respond immediately with a diagnosis, treatment recommendations, or a request for further information. Alternatively, the information can be stored in a dedicated database for later diagnosis by a diagnostician, or in a general database for review and suggestions from any practitioner who uses the invention.

Following treatment, the service provider transmits diagnostic and procedure codes to the system. Insurance coverage for the services provided is then calculated. This calculation may be performed at any appropriate device on the network, including a remote terminal, portable personal device, service provider's computer, network server, or host computer. If the service recipient has multiple insurance carriers, or if insurance deductibles apply to the services provided, the service provider's records are updated with the appropriate billing parties and amount chargeable to each.

Each insurance carrier can be electronically billed for the amount charged to that carrier. The insurance carrier can then pay the bill by electronically transferring funds to the service provider's account at a specified payment interval. Payment histories can be also be electronically transferred from the insurance carrier to the service provider.

The charges to the service recipient can also be calculated by the system and transmitted to the service recipient through the remote terminal, provider terminal, or portable personal device. Thus, the service recipient can be advised of the total charges, amount of insurance charges, and the amount for which the service recipient is liable prior to authorizing any treatment.

In the preferred embodiment of the invention, administrative information transfers are transmitted to the centralized host system during non-peak times. Thus, invoices, appointment lists, messages, and payment records may be transmitted, for example, at night. Batch transfers are preferably used in appropriate instances for high-volume, non-critical information transfers to reduce bandwidth overhead and network contention. However, on-line access approaching twenty-four hour, seven days per week is available for service recipient record access and updates. Emergency and critical information transfers are thereby supported.

The invention facilitates information retrieval and analysis for research. Service recipient historical records stored on the system can be accessed by researchers for full data analysis. Such historical records can be stripped of identifying information before being distributed to researchers.

Research requests can be sent to the system, and run, for example, during non-peak processing times to minimize system resource contention. Data can then be returned to the requesting party through the party's communication link. The invention supports research requests for analysis of any of the elements of the system, such as for analyzing legal compliance or disease management.

In the preferred embodiment, data can be stored in a relational database. Keys such as subscriber identification number, insurer identification number, prognosis, and treatment codes can be used to index this relational database. In the preferred embodiment, the service recipient record data is chronologically indexed to create a continuous history of the service recipient's health care.

The contents of a service recipient's record can include, for example:

(1) uniform core data elements;
(2) standardized coding systems and formats;
(3) common data dictionary; and
(4) information on outcomes of care and functional status.

The core data elements are a set of information fields defined in accordance with federal and international standard setting organizations. These include standard codes for diagnoses, procedures, medications and other elements of health care, standard identifier information for service providers and insurers, and standard data formats for maintaining and transmitting record information. All data elements and their coded values and textual descriptions are maintained in a common data dictionary, which is one of a shared set of platform services used by all system components during processing. (See, for example, FIG. 9).

Records for each service recipient served by the system are stored in a Subscriber/Medical history database. All personal and health care records are included in this centralized database. These records include standard codes for all plans/benefits for which the service recipient is a participant. These codes are used to link to a Plan/Benefit database to access detailed records of a service recipient's coverage.

The service provider standard codes, defined under the Plan/Benefit database record, are used to link to detailed information maintained in a service provider database. In this way, standardized codes are used to access records throughout the system. These records can therefore be maintained at a single location, improving access and eliminating error-prone multiple entries.

Service records within the service recipient's Subscriber/medical history record are preferably stored in chronological order. These records can contain multiple fields relating to the episode, care, outcome of care, and functional status. The personal information device of the service recipient can hold either a selected subset of the full service recipient record or the full record. In the preferred embodiment of the invention, the available storage parameters are used by the system to define a critical subset of the service recipient record to be stored on the card.

In the preferred embodiment of the invention, a standardized, patient-oriented health care record with display of service recipient identification and emergency information followed by sequential episodes of care is used as a default format for service provider and service recipient access. This default format can be displayed as a screen display or graphical user interface (GUI). A customized screen display can also be provided to meet the specific needs of a system user. This GUI can present the standardized health care record for the service recipient as it is downloaded from the individual information device or from the total record stored in the Subscriber/Medical history database. This standardized health care record can include:

(1) A structured, systematically collected database of service recipient health care records constructed at the point of service and collected during the service process;

(2) An easily reviewed and updated problem list using standard diagnostic codes. Definitions can be updated and new diagnostic, procedural and medication codes created and stored in the central records;

(3) Records of clinical formulations and plans for care and follow-up can be stored in the central host databases for use, for example, by all research organizations and agencies in assessing care components.

In addition, intelligence built into the system includes decision support, clinician reminders, and customizable "alarm" systems as explained below, in detail, in AI Medications/procedures. Multiple standard reporting formats, such as hard copy reports, and billing and payment reports, are also available to all clients on a daily, weekly, monthly and annual basis.

In the preferred embodiment of the invention, all central host databases use a standardized common data dictionary to ensure standardization of all system database elements. The common data dictionary can store field definitions, acceptable codes or values, edit rules, format rules, data owner showing who has ultimate authority to issue updates and revisions to the field. The data dictionary fields can also contain references to other diagnostic, procedural, pharmaceutical and personal information codes to identify potential incompatibilities or problems.

This data dictionary can be used in the processing of changes to the databases and in the construction of research requests. In addition, a database, such as the Medications/Procedures database can access the data dictionary codes when responding to a query. The data dictionary can then be used to limit the information retrieved in response to the query to those cases containing no potential incompatibilities or problems. In this way, the information stored in the data dictionary can be used to enable other functional capabilities of the system.

The lists of standardized codes for all prognoses, medications and treatments are centrally controlled. Full cross element edits are included to flag potentially invalid or incorrect entries. The values in the data dictionary can be used to construct a customized edit of a service recipient record. The use of such common data dictionary, standardized coding schemes, and uniform data sets promotes complete, reliable analyses of care and disease patterns.

This invention employs the use of open standards promulgated by standards organizations. Such open standards include the open standards defined for hardware, software and firmware components. For example, use of the open standard for integrated circuit cards can significantly reduce the cost of card production, and increase the availability of compatible components, such as card readers. Additionally, use of the open standard can enable the card to carry other value-added consumer information regarding additional services, products, organizations and corporation.

Customized GUI formats implementing such standard elements can be configured to follow the standards of different specialties, for example, as defined by the American Medical Association or other specialist and international organizations. Technology support standards from unified representation, such as those developed by the National Institute of Standards and Technology and the International Standards Organization's (ISO) Open Systems Interconnect (OSI) model can also be implemented.

A standardized vocabulary developed from unified representation, such as the Systematized Nomenclature of Medicine, the Read Clinical Classification in Great Britain, the ASTM Standard Guide for Nosologic Standards and Guides for Construction of New Biomedical Nomenclature and the National Library of Medicine's UMLS project, can be used with the invention. The preferred embodiment of the invention also supports the use of standardized formats for health care data interchange from unified representation, such as HL7 (Health Layer 7), an American National Standards Institute (ANSI) accredited standards organization, ANSI X12 electronic data interchange formats for health care information communication (published by the Data Interchange Standards Association, also known as DISA), National Provider Identifier and PAYERID (initiatives of the US Health Care Financing Administration for identification standardization for service providers and health care payers, respectively), Institute of Electrical and Electronics Engineers (IEEE), Medix, standards for transfer of clinical data from the American Society for Testing and Materials, and the American College of Radiologists/National Electrical Manufacturers Association standards for image transfer.

The system software is designed as a distributed model with software modules stored at either their point of use or point of access. The central host(s) preferably maintains the central databases, data dictionaries, centralized communication functions for informational updating, routing and messaging, centralized servicing including database maintenance, remote systems management, customer servicing, funds transfer processing, data warehouse querying, statistical analysis processing, exception processing, record and processing overrides, and service billing and accounting applications.

For service providers, a server can store subsets of the central databases, applications for performing batched update functions, and software modules for accessing functionalities of other system components. This model allows localized sharing of data among service providers operating within a single administrative setting, for example, within a hospital or clinic, without the delays and additional costs of continual central host accesses. Restricted local and unrestricted system-wide uses can therefore be implemented.

In a single terminal embodiment of the invention, the terminal (for example, the provider terminal, or a personal digital assistant) can store subsets of the central databases, applications for performing batched update functions, and software modules for accessing functionalities of other system components. In addition, the terminal stores the applications required to access and transfer information to and from the individual information device.

For the other functional users of the system, the applications for performing the various users' processes can reside on the users' local computers or localized server configuration. Alternatively, any subset of the software applications, such as communications and security software only, can be stored on the user's computer, while additional applications are accessed from the central host/server. In all cases, records for all databases are accessed and stored at the central host.

The invention provides security for restricting access to the system to an authorized user. The types of security supported by the invention include password protection, encryption, and identification authentication. This security is provided by a security module within the user's computer or individual information device and used in conjunction with passwords. Information regarding such security attributes and procedures can be stored in a security management shared platform service for use by all system processes and components.

The invention can be used in conjunction with data storage, backup, and restore mechanisms to safeguard records in the event of system failures. These system management features are included within the Applications/Management shared platform services and are used by all central host databases. Personal or networked computers used by various system users can be customized to provide remote or local data backup, archive and restore capabilities. Additionally, data can be fully restored from the files of the central host(s).

Figure 3:
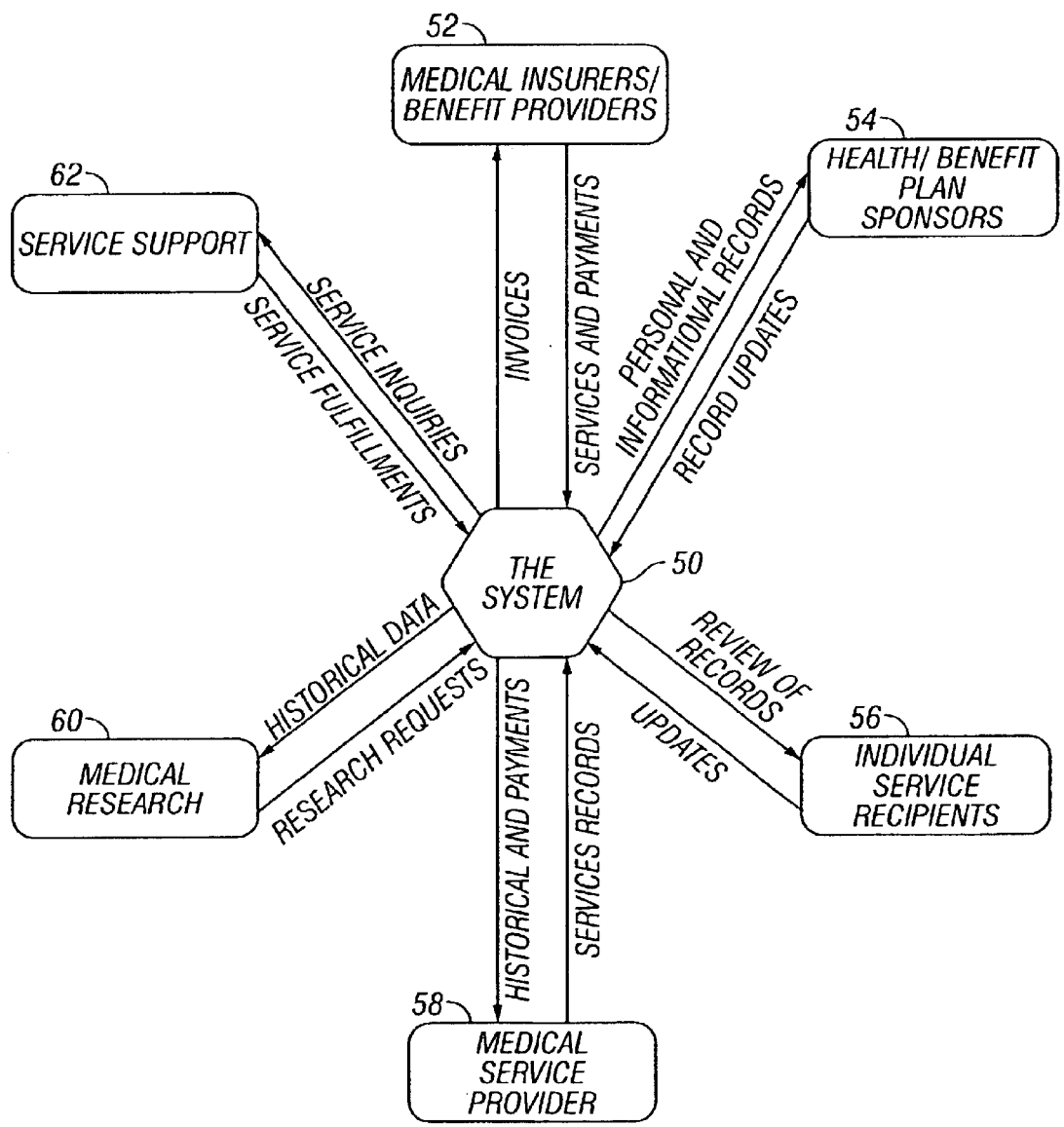
FIG. 3 is a context diagram of the system for consolidating and distributing information, according to the preferred embodiment of the invention.

FIG. 3 is a context diagram of the system for consolidating and distributing information, according to the preferred embodiment of the invention. This diagram shows the primary functional areas of the system and identifies the users of each functional area. The system 50 links together functional areas such as Medical Insurers/Benefits Providers 52, Health/Benefit plan sponsors 54, individual service recipients 56, health care service providers 58, Medical Research 60 and service support 62.

Medical Insurers/Benefit Providers 52 include:

(1) benefit managers;

(2) federal, state and private insurers;

(3) business health care coalitions;

(4) employers who self-insure or manage their own benefits packages; and (5) annuity and retirement account management organizations.

Processes supported by the invention include plan definitions. In such plan definitions, an insurer defines a new plan or changes an existing plan, including coverage options, geographic coverage, lifetime treatment limits, support features, procedures and medications covered, service providers and/or categories of services provided, limitations on groups or individuals applying for coverage, automated authorization of benefits, service recipient automated referrals, service payment accounting with payment service network integration, providing communication in the event exception processing is required, and reporting and statistical analysis. Changes in plan definitions can be automatically communicated to current service providers and plan sponsors. Plan definitions can also include open enrollment marketing features. Such open enrollment marketing features can include features supporting simplified design of an on-line plan summary for accessing the plan definition information within the central host database and for responding to plan sponsor requests for contact, and update methods for adding, deleting and changing service recipient plan participation records.

All health care program providers are identified within, and electronically linked to, the system and are therefore provided with up-to-date information. Thus, problems associated with service provider status are avoided. For example, the service recipient or referring service provider is informed when a provider ends its affiliation with a care plan and can therefore select another, affiliated provider.

The invention also can reduce the costs of publishing and distributing directories of caregiver information. New medical insurer/benefit provider defined plans are communicated to providers and to plan customers automatically by the central host as the plans are implemented, changed or discontinued. Thus, all customers and suppliers of an affected plan are aware of changes in plan coverage.

Health/Benefit plan sponsors 54 include:

(1) health and benefit plan management staff; and (2) human resource department staff.

The processes supported by the invention include support of open enrollment, in which the medical insurer/benefit provider creates a record within the Plan/Benefit database specifying plan parameters (detailed information on plan coverage) which are accessible to plan sponsors, service recipients and service providers through features of the full system. These processes allow plan sponsors to search for new applicable plans, and allow service providers to investigate new service relationships.

Changes to existing plans, are automatically communicated to plan sponsors and service providers with current plan relationships, by the central host. When changes are made to existing plans, the Medical Insurer/Benefit Provider can request, during the queuing of the update file to the central host, that current service providers and plan sponsors be notified by an electronic message of the changes to the plan. This is described below, in detail.

Individual service recipients 56 include health care and benefit consumers such as:

(1) service recipients; and (2) service recipient family members.

Processes supported by the invention include updating records and messaging. Such messaging services can include electronic mail (e-mail), voice mail, and paging. Service recipients can review the contents of their health care record and its associated payment history, identify errors and omissions therein, and include treatment plan preferences.

The invention permits service recipients to search the Artificial Intelligence (AI) Medications/Procedures database regarding treatment options and medications and procedures information, and search the Subscriber/medical history database toward development of a care contact network. The invention also supports health plan enrollment and use by providing features allowing service recipients to review plan coverage parameters and service provider networks affiliated with health plans offered by their plan sponsor. Communication to all members of a service recipient's health care network are supported by the system.

Medical service providers 58 include:

(1) alliances, associations, networks and systems of providers;

(2) ambulance services;

(3) ambulatory surgery centers;

(4) donor banks including those for blood, tissue and organs;

(5) health maintenance organizations;

(6) home care agencies;

(7) hospices;

(8) hospitals;

(9) nursing homes;

(10) preferred provider organizations;

(11) physician offices;

(12) psychiatric facilities;

(13) public health departments;

(14) substance abuse programs;

(15) dental service providers;

(16) pharmacies;

(17) testing facilities; and

(18) therapeutic care providers.

Functions supported by the invention include accessing service recipient histories and updating service recipient records. Services can be authorized through access to the central host(s). The central host can also calculate, and attach to all pertinent records, the amount of payment required from each of multiple parties, health care history updates (including payment calculations and authorization of services, automated referrals with communication linkages, etc.), AI medications/procedures available for diagnostic and treatment support, and research requests. In addition, the system manages and services payments and record keeping, including automated invoicing for un-reimbursed service recipient accounts.

Medical Research 60 include:

(1) allied health professional schools and programs;

(2) medical schools;

(3) nursing schools;

(4) public health schools;

(5) accreditation organizations;

(6) institutional licensure agencies;

(7) professional licensure agencies;

(8) disease registries;

(9) federal, state and local government policy-makers;

(10) agencies investigating legal compliance;

(11) lawyers;

(12) health care researchers and clinical investigators;

(13) health care technology developers and manufacturers;

(14) health data organizations;

(15) health sciences journalists editors;

(16) research centers;

(17) medicare peer review organizations;

(18) quality assurance companies;

(19) risk management companies;

(20) utilization review and management companies; and

(21) service providers and service recipients.

The needs of the users of this functional area are supported by links to informational databases, statistical reporting applications, and software features for collecting data and constructing customized databases. The use of standardized codes permits the users to readily retrieve information necessary for the long-term analysis of treatment methods and outcome of care.

Service support 62 includes the agencies and staff for updating and maintaining the system, including:

(1) service parameter maintenance;

(2) product support;

(3) customer requests; and (4) system maintenance.

The processes supported by this functional area of the invention include those for performing system maintenance, security, customer service and billing functions and for international, federal or state authorized agencies to automatically update centralized information. Designated agencies such as the Agency for Health Care Policy and Research and authorized organizations such as state licensing review boards can be provided with secure access to the system for updating and maintaining records. Additionally, the system is continually updated to include current health care standards, as well as information regarding all users of the invention.

Licensing and other regulatory information is preferably stored in a service provider record within the service provider database. This information is available to all authorized users of the system and can be updated or used for research requests by regulatory agencies. Security levels are defined within the Security management component of the shared platform of services.

As an example, records for service provider organizations within the service provider database can contain licensing information, staffing affiliations, organizational ownership information and tax identification information required to monitor legal compliance. The service provider records can include the curriculum vitae of a licensed practitioner, as well as information regarding any disciplinary actions against a licensed practitioner or service provider.

Figure 4:
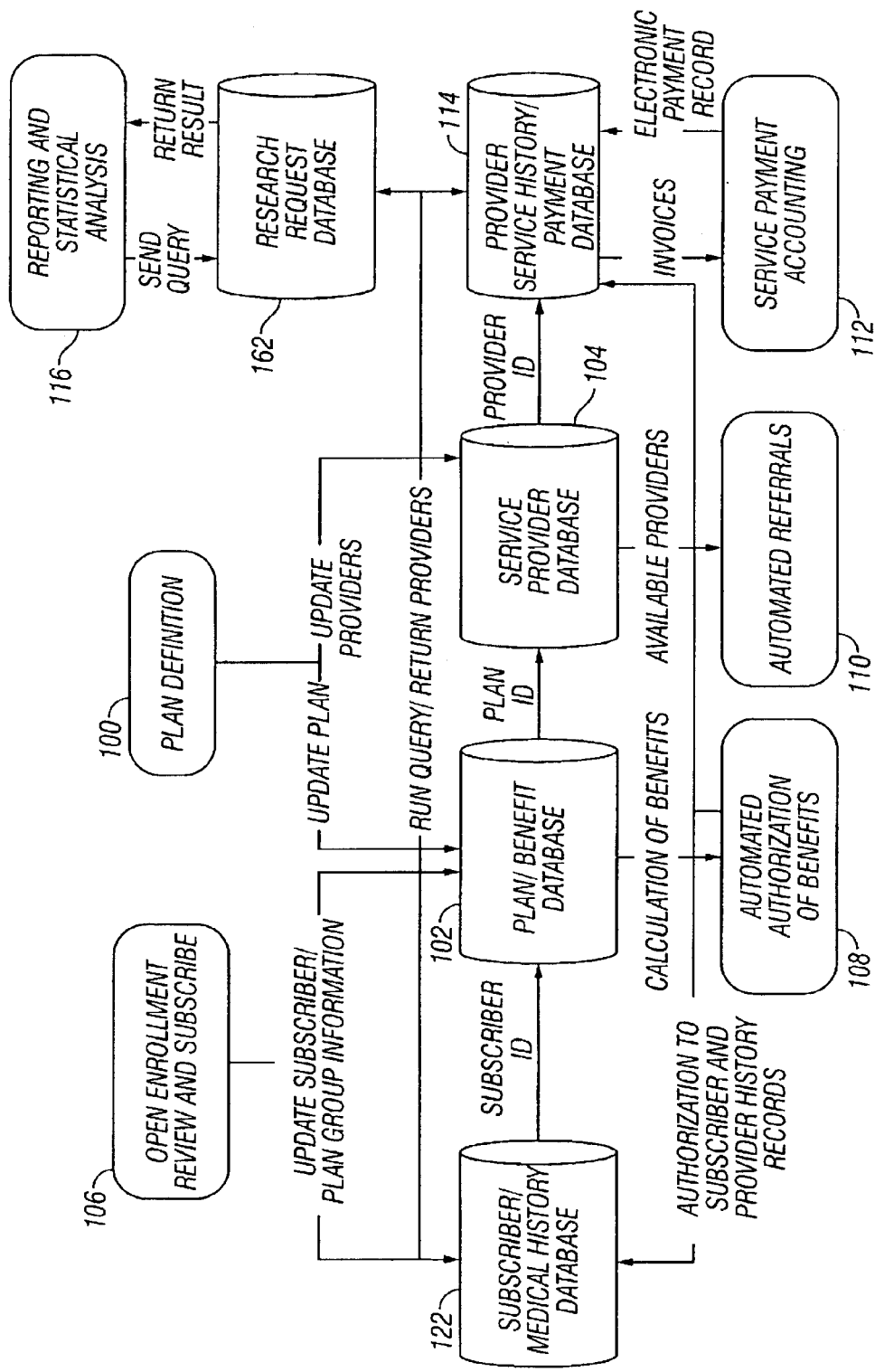
FIG. 4 is a flow diagram of the medical insurer/benefit provider processes, according to the preferred embodiment of the invention.

The medical insurer/benefit provider (see FIG. 3, element 52) functional area supports all aspects of service recipient care reimbursement. FIG. 4 is a flow diagram of the medical insurer/benefit provider processes, according to the preferred embodiment of the invention. Plan Definition processes 100 are available to update medical/benefit plans stored in the Plan/Benefit database 102, located at the central host(s).

The medical insurer/benefit provider accesses the central host(s), and provides required security responses to download current insurer records for the specified plan(s) from the Plan/Benefit and service provider 104 databases. Software applications, preferably operable on the medical insurer/benefit provider's computer, is used to add, update or delete records to/from the databases. Such updates include the review, deletion, and revision of existing plans, as well as the creation of new plans through the setting of new plan parameters. Plan parameters include the identification of procedures, pharmaceuticals, service providers and other care plan components covered by the medical/benefit plan, and the determination of payment and reimbursement ceilings and out-of-network service coverages.

The date on which a change is to occur can be included in the records. Batched update features and copy capabilities for current record information is available to simplify changes to records. The medical insurer/benefit provider computer can access the central host(s) and download an updated file, with any other information regarding implementation dates/times, automated notifications of changes, and whether service recipient records are to be updated with plan changes.

Open enrollment processes 106 are available to support marketing and enrollment efforts for new and current plans by supplying on-line information for access by, and/or automated distribution to, Health/Benefit plan sponsors and their respective service recipients. The medical insurer/benefit provider accesses the central host(s), to download current medical insurer/benefit provider records for the specified plan(s) from the Plan/Benefit and service provider databases.

The medical insurer/benefit provider then can construct or change the plan marketing information. When all changes have been completed, edited and audited, the updated file is downloaded to the central host(s).

Health/Benefit plan information is available to potential customers, for example, through non-solicited searches by other service providers, plan sponsors, and service recipients for other available plans. Potential Health/Benefit plan sponsors or service recipients can review the information and communicate with the medical insurer/benefit provider's marketing and sales staff. Potential service providers can also apply for inclusion in a plan by communicating with the medical insurer/benefit provider.

When a plan sponsor elects to participate in a new plan, to change plan record information, or to drop participation in a plan, the medical insurer/benefit provider updates the Plan/Benefit database with plan sponsor information. In addition, the medical insurer/benefit provider can update the subscriber/medical history database when new subscribers/service recipients are enrolled or changes are needed to a subscriber/service recipient's record.

The medical insurer/benefit provider accesses the current Plan/Benefit records from the Plan/Benefit database stored on the central host(s), and/or subscriber/medical history records from the subscriber/medical history database for the specified plan sponsor group(s). These records can then be reviewed, modified, or deleted, as desired.

In the preferred embodiment of this invention, a field indicator on the subscriber/service recipient record can be used to request a new or replacement individual information device.

Automated authorization of benefits 108 is also provided by the invention. When authorizations for services are submitted by a service provider during the Update Medical History process, a record containing service recipient identification and plan information, service provider identification, and procedure and/or medication codes is transmitted to the central host(s). The central host tags the request with a unique authorization request number, verifies the service recipient plan information from the subscriber/medical history database, and verifies status of the service provider.

The request is then compared to plan coverage information parameters for the affected plan(s) from the Plan/Benefit database. If multiple payers are involved, payment amounts are calculated for all affected parties. An authorization record is created in the provider service history/Payment database and in the subscriber/medical history database.

The applicable approval codes and payment amounts are added to the service provider authorization record. The authorization record can contain standard formats and codes of international standard setting organizations, such as 837 Health Care claim Process in X12 from the Data Interchange Standards Organization. When a request for authorization is declined, due to parameters of the plan, the central host(s) transmits an on-line decline message to the medical insurer/benefit provider and the service provider. A manual review procedure for handling exceptions, appeals and questions can then be initiated.

Patient automated referrals 110 identifies specialist service providers, hospitals, and clinics participating in a Health/Benefit plan, as defined in the service provider database 104. If, during the Update Medical History process, the service provider wishes to refer a service recipient to a specialist service provider, hospital, clinic or other referral organization, a referral request is transmitted, along with service recipient plan information, from the service provider computer to the central host(s).

The central host(s) uses these codes to construct a search of the service provider database. Search results are returned to the requesting service provider for display in a selectable GUI on the service provider computer. The service provider can then select the record for the desired referral provider.

The service provider database search can be limited to in-plan providers. Alternatively, the service provider can perform a geographic or affiliation search, or can identify a specific targeted referral provider. The service provider can then perform a service authorization, as defined above.

Authorization approval is returned from the central host to the service provider computer. A message requesting an appointment for the service recipient, including the phone number to call for scheduling can be automatically constructed and transmitted to the referral service provider.

The preferred embodiment of the invention provides accounting services 112 to users. Such accounting services include the transmittal of invoices from a provider service history/payment database 114 to the medical insurer/benefit provider. Payments of these invoices may be made electronically, with funds transferred directly from the medical insurer/benefit provider's account to that of the service provider.

The medical insurer/benefit provider can identify specific accounts from which a payment is to be made, and can record the date of the payment and information regarding its transfer. A payment history can also be generated and stored in the provider service history/Payment database 114. Such payment history can then be appended to the service recipient's medical history.

The medical insurer/benefit provider accesses the central host(s) to retrieve unpaid provider service history records for the specified plan(s) from the provider service history database. If desired, current plan and provider information can be retrieved from the Plan/benefit and service provider databases.

Software applications operable on the medical insurer/benefit provider's computer are used to approve records for payment. Account information from the service provider database can be used to define the electronic funds transfer parameters. Records can be batched into folders for operational handling purposes, and electronic and printed audit reports can be generated. The payment record can contain standard formats and codes of international standard setting organizations (such as 837 Health Care claim Process in X12 from the Data Interchange Standards Organization).

If exception items are identified, an exception handling message can be constructed and prepared for routing, using the parameters of the service provider record, including communication addresses. An updated file is transmitted to the appropriate database(s) on the central host(s).

The invention supports reporting and statistical analysis processes 116 for information stored in the subscriber/medical history, plan/benefit, service provider, and provider service history/payment databases 114. Such processes include providing reporting and statistical information for service provider monitoring, and providing service data for benefit calculations.

Organizational summaries can be generated for use in developing practice guidelines. Practice guidelines are systematically developed statements for assisting practitioner and patient decisions regarding appropriate health care for specific clinical conditions. Organizational summaries can also be generated for use in outcomes management. Outcomes management is the assessment of ultimate results of efforts to prevent, diagnose, and treat various health problems.

A statistical analysis of the cost and outcomes of care information can readily be performed to assist a service provider in budgeting decisions. Full service recipient care information can also be electronically provided for use in adjudicating of claims and making coverage decisions. The medical insurer/benefit provider accesses the Research Request database 162 on the central host(s) to download data dictionary information for the central host databases, including the subscriber/medical history 122, Plan/Benefit 102, service provider 104 and provider service history 114 databases. This information can be stored on the medical insurer/benefit provider's computer, as desired.

The medical insurer/benefit provider can then use software operable on the provider's computer to construct a data query. Desired data fields are selected from the data dictionary of the central databases, ensuring from the rules in the data dictionary that appropriate authority is available for access to the data. Security rules limit access to certain fields, and requests for non-authorized data are returned from central host processing with a security restriction message.

Data queries can be specified as one-time only or can be requested on an ongoing, time-specific basis for continuing research efforts. When all data queries have been completed, the request file is transmitted to the central host(s) and the data search is performed. The search results, or an error message, is then returned to the medical insurer/benefit provider.

Figure 5:
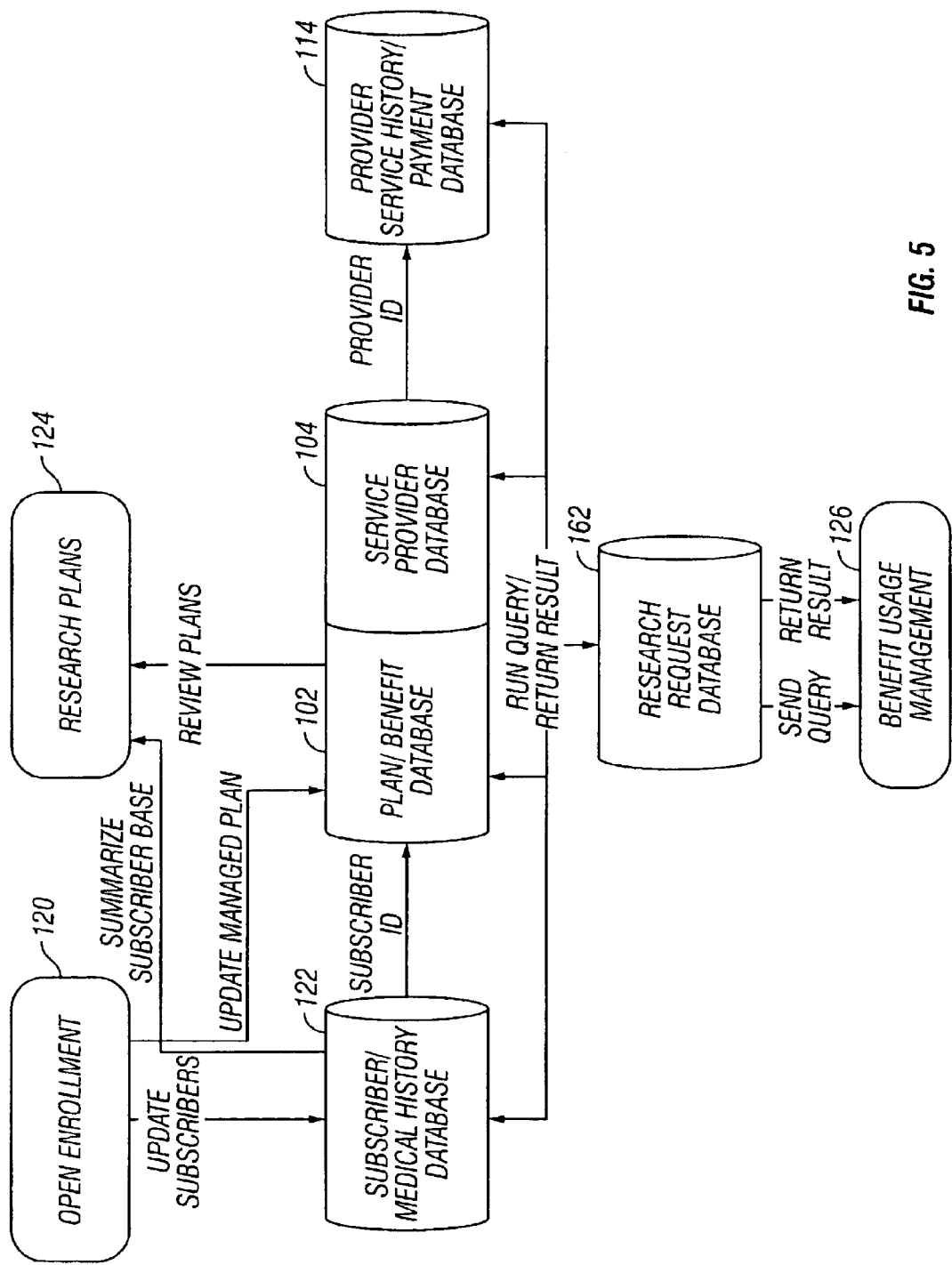
FIG. 5 is a flow diagram of the Health/Benefit plan sponsor processes, according to the preferred embodiment of the invention.

The Health/Benefit plan sponsor (see FIG. 3, element 54) functional area of the invention supports Health/Benefit plan management staff and human resource department staff. FIG. 5 is a flow diagram of the Health/Benefit plan sponsor processes, according to the preferred embodiment of the invention.

Open Enrollment processes 120 are available to support changes to currently sponsored benefit plans and to support requests for the production and distribution of individual information devices. These changes are implemented through access to the central host, as described above.

Modifications can be made, for example, to change benefit information, such as additions, changes or deletions to auxiliary reimbursement accounts, insurance, annuity, retirement or workman's compensation plans, in the Plan/Benefit database. These changes can be made manually or electronically. Modifications can also be made to plan participation records in the subscriber/medical history database.

Production and distribution of new or replacement individual information devices can be requested by the medical insurer/benefit provider. In this way, requests for new devices, for replacement of existing devices, and for deactivation of devices are transmitted electronically through the central host(s) from the Health/Benefit plan sponsor to the authorizing medical insurer/benefit provider.

When all changes have been completed, the updated files are transmitted to the central host(s). The central host can then distribute these updated files to the various components of the system.

Research plans processes 124 are available to permit plan sponsors to search for available applicable plans within the Plan/Benefit database. Plan sponsors are also able to review and compare available plans and to communicate with a medical insurer/benefit provider to apply for inclusion in a new plan. In addition, when medical insurer/benefit providers add or update plans, electronic notification is automatically sent automatically to affected parties.

The electronic communication features support exception item processing and dispute resolution among medical insurers/plan sponsors, service providers and service recipients. This is accomplished by allowing the plan sponsor to copy records involved in the exception or dispute from the subscriber/medical history database, Plan/Benefit database and/or service provider database into a message for involved parties. This message can include text supplied by the plan sponsor.

The plan sponsor accesses the central host(s) to retrieve electronic messages or download previously requested files, review available plans on-line, send electronic messages constructed on-line or off-line, and/or submit a request for access to applicable records from the central host databases. This information can be stored on the plan sponsor's computer for later use.

The plan sponsor can then construct a search for applicable new plans by loading subscriber/medical history records into a summary criteria data query format GUI. This information is transmitted to the central host(s) to, for example, create a search for other applicable plans, review plan information, request marketing information, or respond to plan and coverage issues.

Benefit usage management processes 126 allow the Health/Benefit plan sponsor to access information stored in the subscriber/medical history 122 and Provider/Service History 114 databases. This information can then be used for management of medical care reimbursement accounts, workman's compensation or other auxiliary plans. The Health/Benefit plan sponsor can also use this information to respond to queries on service participant benefit selection and usage, service audits and information for tax and reporting purposes.

The plan sponsor accesses the central host research request database to download data dictionary information for central host databases, including subscriber/medical history 122, Plan/Benefit 102, service provider 104 and provider service history 114. This information can be stored on the plan sponsor's computer for later use, for example in constructing data queries. Data queries can be specified as one-time only or can be requested on an ongoing, time-specific basis for continuing efforts, such as electronic transmission of data to reimbursement plans on a regular basis.

Figure 6:
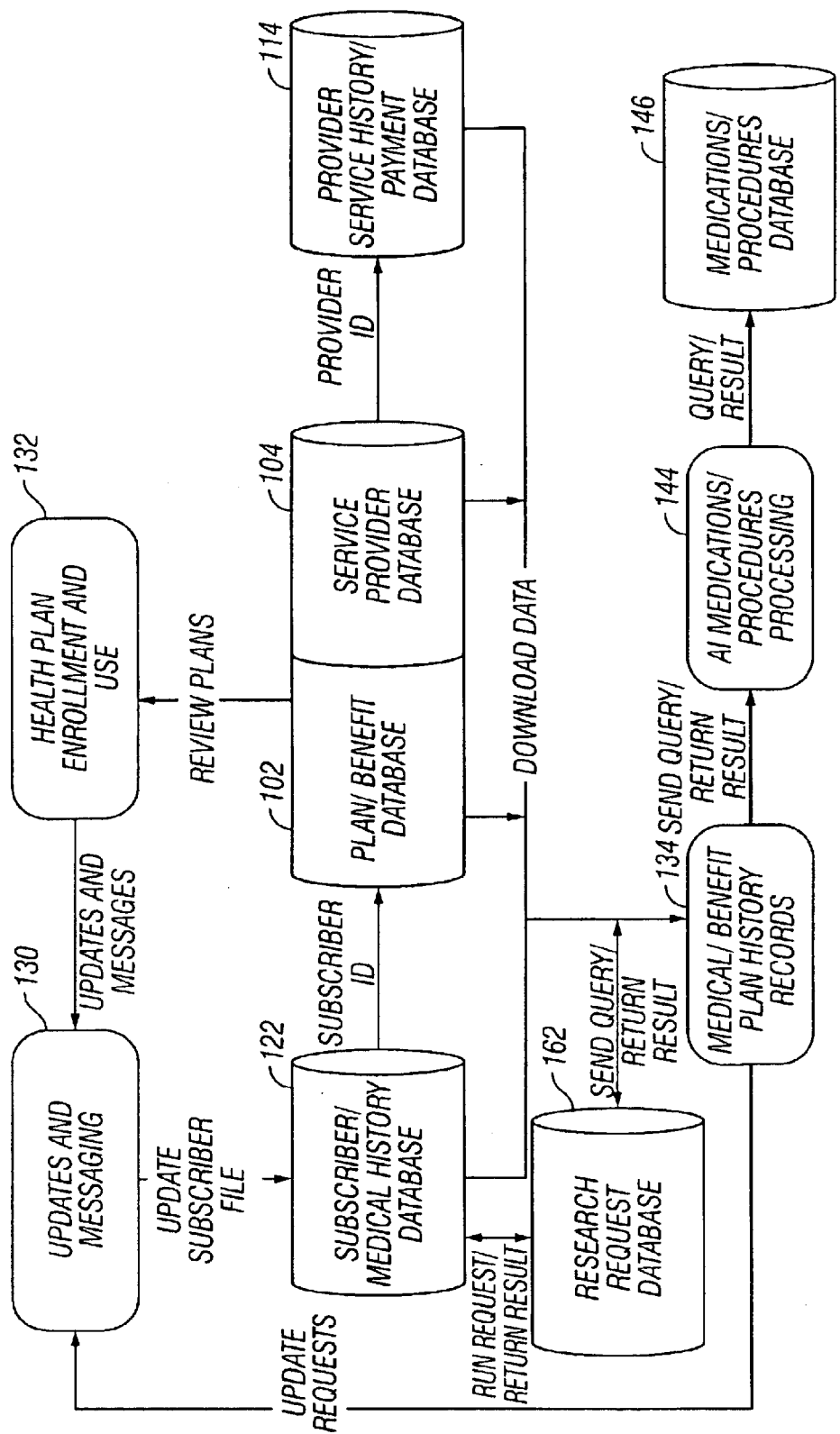
FIG. 6 is a flow diagram of the individual service recipients processes, according to the preferred embodiment of the invention.

The individual service recipients (see FIG. 3, element 56) functional area of the invention supports service recipients, their families and dependents. FIG. 6 is a flow diagram of the individual service recipients processes, according to the preferred embodiment of the invention.

A service recipient is provided with an individual information device which holds identification and critical care information. In the preferred embodiment of the invention, this individual information device is an integrated circuit card, also known as a Smart Card.

The individual information device stores a summarized health care history of the service recipient. This summarized history is available to service providers in the event of a health care emergency and can be readily updated through the electronic network. The summarized health care history can include information regarding chronic health conditions, allergies to medications, medications currently prescribed, and emergency family contacts.

For example, a paramedic providing emergency health care treatment to the service recipient can use the individual information device to review the service recipient's diagnostic and treatment history, emergency contact information, allergy and other critical information and plan coverage records through the use of a portable reader device. In addition, a paramedic having access to the central host can use the host's diagnostic features, in conjunction with the service recipient record, to aid diagnosis of a problem and isolate a possible course of emergency treatment.

The electronic health and personal record eliminates the need for a service recipient to fill out paper forms at a service provider office or to try to remember episodes of care and the affiliated dates. Also, the automated service and authorization features of the central host(s) eliminates the problems of selecting referral service providers covered by the service recipient's plan(s), and identifying payment responsibility for treatment. Further features allow service recipient's access to health care treatment option information (through access to the AI Medications/Procedures 144 features) and allow service recipients to create a care network by communicating with others who currently or have previously suffered from similar health care diagnoses.

Updates and messaging processes 130 allow the service recipient to communicate with health care providers such as practitioners, insurers, and sponsors. The service recipient can access the central host to electronically research care options provided under the service recipient's Health/Benefit plan and access expert health care databases.

Electronic messages can be retrieved, previously requested files downloaded, available plans reviewed on-line, and electronic messages sent. Requests can be made for access to applicable records from the central host databases. Plan/Benefit information can include information about other types of benefit plans, including reimbursement accounts, insurance, annuity, retirement or workman's compensation plans.

The service recipient can use this information to review plan information, treatment and payment histories, construct messages to a plan sponsor for replacement of an individual information device, or ask questions regarding plan options or usage. The service recipient can also initiate changes in the recipient's medical history record. Such changes can include emergency, allergy, contact, identification or treatment preference option information, notations on functional health status or errors found in the health care history record during an audit. Messages can be sent to service providers regarding questions, treatment options, or requests for appointments. Messages can be sent to medical insurer/plan sponsors regarding questions, coverage issues, payment records, dispute resolution, regarding research queries on diagnostic options or for contact information. For all processes completed while operating in an off-line mode on the service recipient's computer, the service recipient repeats the process described above to connect to the central host(s) and collect and transmit new messages.

Health plan enrollment and use 132 processes provide access to health plan information during open enrollment periods. The service recipient can periodically access the Plan/Benefit database 102 to review changes to plan parameters such as approved procedures, pharmaceuticals, providers, payment/reimbursement ceilings, and out-of-network services coverage parameters.

For example, information on multiple plans for health plan enrollment evaluation can be loaded into a comparison form at the service recipient's computer to provide a feature by feature comparative analysis of available plans and their respective treatment options, coverage limits, service providers, etc. This information can be used to construct messages and requests to medical insurer/benefit providers, service providers or plan sponsors for further information, clarification or action. For all processes completed while operating in an off-line mode on the service recipient's computer, the service recipient repeats the process described above to connect to the central host(s) and collect and transmit new messages.

In the preferred embodiment of the invention, medical/benefit plan history records processes 134 are available to access information pertaining to their care or the care of their family members which are stored in the central host databases including the subscriber/medical history 122, Plan/Benefit 102, service provider 104 and provider service history/Payment 114 databases. The service recipient can therefore review allergies and emergency information, health plan status, identification, and emergency contact information, health care history records and service history/payment records. Information from the subscriber/medical history record can be formatted into a health care history and subscriber information record. The service recipient can "flip through" these records, allowing an audit of current services, diagnoses, procedures and medications, and payment histories. Messaging features are also supported.

Using a service recipient features GUI, the service recipient selects a message option, and identifies a selected plan sponsor (if there are more than one). The system then constructs a message form which the service recipient can use, for example, to request replacement of an individual information device, change personal records, or ask questions regarding plan options or usage. This message can be transmitted through the central host(s) during the service recipient's next on-line session.

Changes to the service recipient's health care history record are implemented by selecting an information history change or addition option to note changes, for example, to emergency, allergy, contact, identification or treatment preference option information, notations on functional health status (such as current condition updates for health monitoring like results of home testing on a regular basis) or to correct errors found in the health care history record during an audit. These changes will be routed to central host(s) database administration during the next on-line session.

A construct message option permits the service provider to communicate, for example, questions, requests for appointments, queries regarding functional health status and results of administration of home tests. Information relating to the request and additional notes and comments can be append to a communication. A construct search option permits searches of system records.

An additional formatting option allows the service recipient to use health care information and payment records to construct printed reports, including IRS accountings of health care services and costs during a given tax year, listings for health care reimbursement plans, or general health care information records.

Artificial Intelligence (AI) Medications/Procedures 144 processes allow the service recipient to review results of consumer queries regarding procedures, medications, and other care components from a constructed search of the AI Medications/Procedures Database. This database maintains information on current treatments and medications, including company names and cost information. The database may also include descriptions of diseases and information regarding their causes, as well as preventative advice or health maintenance information.

Supported AI medications/procedures processes include database searching, and messaging. In the preferred embodiment of this invention, these service recipient features are off-line processes, thereby reducing contention on the central host databases. However, an alternate embodiment of the invention supports direct connection and on-line searches by the service recipient of the Medications And Procedures database 146, as well as access to records in the other central host databases.

Figure 7:
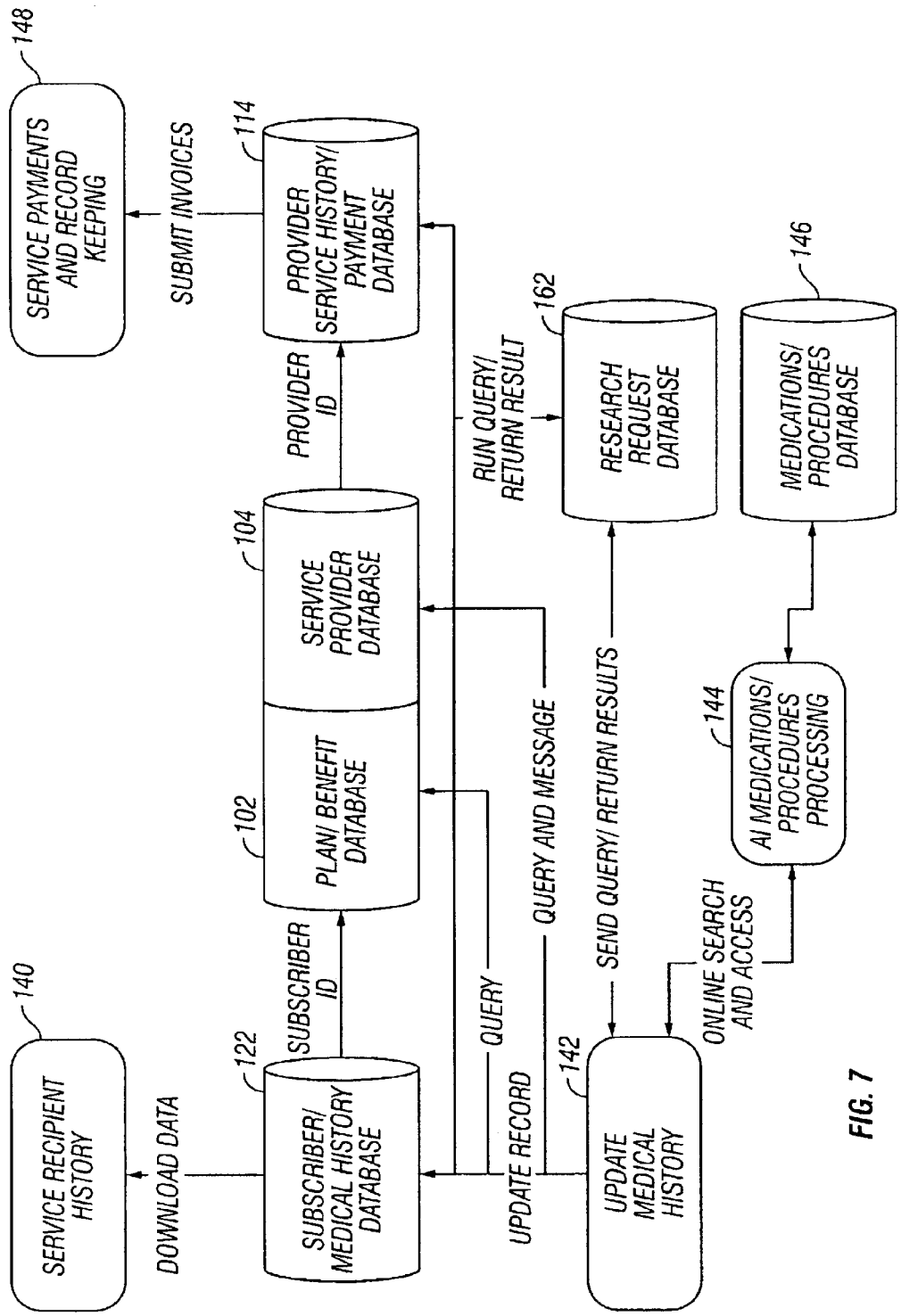
FIG. 7 is a flow diagram of the health care service provider processes, according to the preferred embodiment of the invention.

Health care service provider processes support private health care practitioners, service recipient care providers, health care delivery organizations, hospitals, and emergency health care services. FIG. 7 is a flow diagram of the medical service provider processes, according to the preferred embodiment of the invention.

Service recipient history processes 140 support the review of health care history records stored on the service recipient integrated circuit card and, for a full and detailed record, on the subscriber/medical history database 122. Portable devices, such as mobile units can be used to access emergency information stored on the service recipient individual information device. Such access can be made either on or off-line.

The service provider swipes the individual information device through an attached card reader. If the service provider is operating in an on-line mode, the service provider accesses the central host(s), provides required security responses, and transmits identification parameters from the ICC record, which identifies the full record on the central host(s) subscriber/medical history database and downloads the full record.

If the service provider specifies a request to download diagnostic codes, software operable on the service provider's computer allows the service provider to identify categories for selection of appropriate detailed diagnostic codes for use during the consultation. These codes, along with the service recipient record, can be transmitted to a hand-held or digital personal assistant device if desired, or can be printed for use during the examination. Full diagnostic code sets can also be resident on the service provider's server, downloaded with other batched transfers, if a larger volume computing configuration is being used by the service provider.

Once available, the full service recipient record is loaded into software operable on the service provider computer, which formats the record into a desired screen format, which can also be printed. This format can be of a standard problem-oriented medical record, time-oriented medical record or any other customized format, as selected by the service provider. Diagnostic, procedural and medication codes are shown with their definitions, as available through the central host(s). These codes can be downloaded at any time and stored for further off-line usage.

In addition, all codes for medical plans/benefits can be shown with full textual code descriptions in the language specified by the service provider. Service recipient information contains a detailed health care history including procedures and medications and dates of both, emergency, allergy, contact and identification information, insurance information, functional status, treatment preferences and comments and changes to history as noted by the patient.

An on-line help feature can also be provided to facilitate service provider use of the invention. The on-line help is a file on the service provider's computer which can walk a caregiver through the process of accessing and loading information from any source, whether the ICC record only or steps involved in accessing the central host(s) subscriber/medical history database and performing the operations of accessing, downloading and using diagnostic codes.

These steps allow the health care service provider (see FIG. 3, element 58) to quickly access a list of current problems, a trail of clinical logic, the service recipient's health status, and the most recent information about various treatment options for the service recipient's condition. The health care provider's rationale for clinical decisions can also be accessed. In the preferred embodiment of the invention, routine service recipient care, organizational operations and decision making processes are supported. In addition, since all consultation records are stored in the subscriber's medical history database, health care service providers can avoid requesting redundant medical tests for a service recipient.

In the preferred embodiment of the invention, the service provider's computer software supports a GUI that simplifies access and extends use of the information, permitting users to analyze, transfer, process and compare information using other standard market software packages which extend the system capabilities. Such simplified access also allows integration of customized local features, such as inclusion of text, tables, graphics, video, animation, and audio display.

The GUI is configurable to display information related to the health care service provider's focus. Thus, the GUI can be configured, for example, to display information related to a current query or problem, organized by date, or organized by symptom. In alternative embodiments of the invention, the GUI is configurable to display any information stored in the subscriber/medical history database, which can be linked by the standard system key identifiers to customized capabilities and features maintained on local storage media or accessed via links to remote network addresses. As an example, a teaching hospital can have video display modules, identified by the standard system diagnostic codes, which allow the service provider to select video diagnostic help through the standard GUI, allowing the service provider to view training steps in a recommended procedure.

The service provider can access the service recipient's health care history and information regarding any potential diagnosis. This information can be printed, or displayed on a computer display, or on the display of a personal portable device. The time spent by the service provider in preparing written records and histories can therefore be significantly reduced.

Using the Update Medical History processes 142, a practitioner can communicate with health care providers, insurers, sponsors and service recipients, provide preventative advice and health maintenance information for service recipient self-care, review service recipient preferences and generate care plans, document services provided, assess and manage the risks of various possible treatments for a service recipient, authorize treatments and care options, authorize referrals within a Service recipient's care network, or send messages to other service providers or organizations.

Using software operable on the service provider's computer in an off-line mode, the service provider uses the service recipient's record from the subscriber/medical history database 122 and the selected diagnostic codes which were accessed and downloaded to the service provider's computer through the Patient History process described above.

Software operable on the service provider's computer provides customized screen record formatting. The service provider uses an update record process to update the service recipient record with information obtained during a current appointment. Test results can be loaded into the service recipient's record manually or through an electronic automated interface into the record, such as through electronic monitoring devices, and other patient care equipment for adding data, images or other formats into the record. Because the service recipient's health care history information is readily updated using the electronic network, a health care service provider can monitor subsequent service recipient care and the reporting of any adverse reactions.

The preferred embodiment of the invention provides links to administrative, bibliographic, clinical knowledge and research databases. If the service provider wishes to review on-line diagnostic information through the AI Medications/Procedures functions, the service provider uses software operable on the provider's computer to select a diagnostic assistance feature which prompts the provider to select symptom codes (as included during patient examination), test results, etc. and to define procedure and medication limitations by noting category codes for allergies, current conditions and medications, or other limiting factors.

General database searches can also be constructed. These queries can be constructed on-line or off-line from the central host(s). To connect to the central host(s), the service provider uses software operable on the provider's computer to access the central host(s), provides required security responses, and transmits the search record to the central host(s). The central host processes the search and returns the result records to the service provider, or in the case of video information links, allows the service provider to view the search results through the communication connection.

The service provider can also use the communication facilities to construct a message to referred specialists for later response. Using software operable on the provider's computer, the service provider can select procedural and/or medication codes to run a conflict search against the service recipient record and, if no conflict is noted, paste the selected treatment/procedure/medication/referral codes into the service recipient record and prepare a request for authorization through the central host(s). If codes resulting in conflicts are used by the service provider anyway, that information is appended to the service recipient record.

In addition, a service provider can construct a research request to the Research Request database 162 on the central host(s). This facility can be used to perform outcomes research on specific diagnostic codes or to identify a care network containing other individuals with the same prognosis as one of their service recipients. Using software operable on the service provider's computer, screen options in the Update Medical History component allow the service provider to construct a research request using a service recipient record, or using individual diagnostic or treatment codes. This record is then transmitted to the central host(s) and the result of the search is returned to the service provider at a later on-line session.

The service provider uses software operable on their computer to construct an authorization for services and/or authorization for referral. This date and time stamped record contains service recipient identification and plan information, service provider identification, and procedure and/or medication codes and referral codes, which are transmitted to the central host(s). The central host(s) tags the request with a unique authorization request number, verifies the service recipient plan information from the subscriber/medical history database, verifies status of the service provider and reads plan coverage information for the affected plan(s) from the Plan/Benefit database, calculates payment amounts for all affected parties if multiple payers are involved, creates an authorization record in the provider service history/payment and subscriber/medical history databases, and returns the numbered service authorization record with approval codes and payment amount notification to the service provider.

If a referral has been requested, the central host(s) identifies service providers available through the service recipient's plan(s) by identifying providers from the service provider database, returning a listing of names with address, phone number, affiliations and other information as an attachment to the authorization. If a plan available to a service recipient covers disability, worker's compensation or other support benefits which apply for the prognosis, this information can also be returned in the record, if requested by the service provider.

If a referral was requested, the service provider can select a service provider from the on-screen returned list, send a message to the selected referral service provider which includes the service recipient record, the authorization message and a request for appointment or any other information.

This referral authorization information can also be printed for action by the service recipient or a staff member at the service provider's location and can cover prescriptions for pharmaceuticals and medications as well as procedures and services.

Negative results of conflict edits that were ignored by the service provider is included on any printed output. If no referral is needed, the authorization is saved in the service provider's computer for later transmittal to the central host(s) during the Service Payments and Record keeping processes. When a request for authorization is declined, due to parameters of the plan, the central host(s) transmits an on-line decline message to the medical insurer/benefit provider and the service provider, which can initiate a manual review procedure to handle exceptions, appeals and questions.

When all health care history update activities have been completed and/or all service recipient payments have been made (defined in Service Payments and Record keeping 148), the service provider can use software operable on their computer to update the service recipient's record on their personal information device. In the preferred embodiment, the service recipient's integrated circuit card is updated by swiping it through the service provider's card reader and downloading the most recent record information.

In addition, information from the service recipient record can be used to print a variety of hard copy reports (as in the case of printed authorizations or prescriptions, as defined above). Software operable on the service provider's computer allows the provider to select a print option which then brings up a list of standardized (and customized) reporting formats, including but not limited to: service authorizations, prescriptions, full health care history record of the service recipient, letters, discharge summaries, evaluation queries, insurance forms, school and camp certificates, trend reports and graphs.

When the service provider uses the on-line diagnostic functions in Al Medications/Procedures, the central host(s) uses the search record sent by the service provider (described above) to construct a query of the Medications/Procedures database. This diagnostic information can be used to assist the health care service provider in determining whether a procedure or medication is, for example, effective and safe, cost-effective, and whether it produces desired outcomes.

A summary of reference information is returned to the service provider's computer, where the service provider selects an item and, if it is a reference only, can choose to see the entire record, including images, video or other forms of multimedia. The service provider can select diagnostic, treatment, procedure or medication codes and electronically add them to the service recipient's record and can run an alert check on the updated service recipient record to identify any elements causing a care or treatment conflict. Alert checks are performed by the central host(s) by running a central host program for a treatment, procedure or medication code against the flag edits for those care components.

Conflicts are identified within the treatment/procedure/medication record by their standard code. These include other medications and procedures currently prescribed to research the effects, dosages, and side effects of medications prior to issuing a prescription, and also covers allergy or personal information such as age and condition factors which can result in complications or treatment incompatibilities. The result of this process is returned to the service provider's computer and displayed visually on the screen and can in addition provide an audio signal, allowing the service provider to select a different care option.

If the alerted care component is kept in the treatment plan for the service recipient, an alert message is included in the service recipient's record and on any printed record of the service recipient's care plan, including prescriptions. These processes are performed on-line to the central host(s) with software operable on the service provider's computer used to search, review results, check for care component conflicts, communicate to others in the health care process, and add search results to the service recipient's record. Information in the AI Procedures/Medication database can only be updated by licensed authoritative organizations with secured access to the central host(s) as defined in Update Medications/Procedures, described below.

The invention permits a practitioner to communicate electronically with other practitioners, either practicing with the same health care service provider or with other Providers using the invention. The health care service provider can use the invention to review service recipient plan parameters, including identification of procedures, pharmaceuticals, referral providers and other care plan components covered by the plan, payment/reimbursement ceilings and out-of-network services coverage parameters. The provider to is thereby assisted in generating an optimal care plan that maximizes the service recipient's coverage.

The preferred embodiment of the invention includes a feature within the central host(s) database processing steps for checking data integrity to ensure that data are not lost or unknowingly corrupted. During the processes whereby new records are added to a database (such as the subscriber/medical history database), data elements are run through edit routines defined within the central data dictionary to ensure that data values are for correct standard diagnostic or procedural codes and that variable values are within correct ranges. If invalid entries are detected, the central host(s) returns a data error message to the service provider initiating the entry which defines the problem with the attempted entry and requests the service provider to review and re-submit the entry.

In this way full data integrity checking is incorporated in database update processing. Also, to ensure unauthorized updates are not made, all data owners have update capabilities limited by their security access. For example, medical insurer/benefit providers are limited to update capabilities for their plans only within the total Plan/Benefit database, the addition of subscribers to their plans in the subscriber/medical history database and adding service providers affiliated to their plans in the service provider database. Records other than their own, or fields within those databases which lie outside their required functions cannot be updated under their security parameters.

These security parameters are also identified within the central host(s) data dictionary. Security parameters such as these are defined for all system users through security management. Unauthorized attempts at information access are logged within the central host(s) Security management platform services. These audit trails are monitored by central host security administration and may be communicated to authorized agencies as defined within the data dictionary security parameters (as an example; breaches of security within the service provider network may be reported to the Agency for Health Care Policy and Research or a delegated security organization).

In the preferred embodiment of the invention, the data dictionary contains one or more acceptable values tables to standardize codes and provide a uniform health care vocabulary. For each element defined in the central data dictionary, valid entries (or acceptable values) are defined and updated as additional categories or new ranges are approved. These values can be defined by authorized expert organizations, such as national health management organizations (such as the Agency for Health Care Policy and Research, the Food and Drug Administration, or other organizations to which these responsibilities have been delegated by legislation or agreement) in determining standardized diagnostic codes and data ranges.

Processes by which this information is incorporated into the central host(s) is defined in Update Medications/Procedures and Update service provider information described later in this document. These standardized codes are what ensures data integrity throughout the data value chain as defined within this document and ensures its universal consistency and therefore its value. Such standard codes are used to link related information within the system, such as health care literature and specialists. Another process of this invention provides uploading of the newly revised time-stamped service recipient care records for updating the central information system and the service recipient's portable information device.

The Service Payments And Record keeping processes 148 of the invention provide documentation of services and automation of service payments, insurance claims submissions, and electronic fund transfers for service payments. Such documentation can include the preparation of periodic accounting reports.

A record of non-reimbursed amounts may also be maintained. An automated billing can therefore be submitted for un-reimbursed services. Payment records can be updated to reflect manually received payments and adjustments to records. The preferred embodiment of the invention provides electronic payment services between service providers and medical insurer/benefit providers (as described from the Medical Insurers' Service Payment Accounting functions earlier in this document. Electronic funds transfer payments are noted on matching records in the provider service history/Payment database 114 and to the matching record in the subscriber/medical history database.

Using the software operable on the service provider's computer, the service provider uses software operable on their computer to access the central host(s) and perform security functions. An audit file of payments made to their provider ID during the last central host payment processing file is downloaded. The service provider can then download full records from the central host(s) under their provider ID from the provider service history/Payment database.

In addition, all or selected subsets of records can be downloaded (such as between selected dates, all records with unpaid balances, all records with recent payments or any combination of the above) for use in off-line administrative processing. Electronic messages to the service provider including communications, exceptions and other exchanges can also be downloaded. The service provider can then disconnect from the central host(s) and can perform account administration functions off-line.

Authorizations for current services (the result of activities described above in Update Medical History) are appended to the downloaded records as they are created. During the day's activities, software operable on the service provider's computer can be used to log payments made by service recipient or other adjustments to service/payment records. In addition, if the service provider wishes to perform a manual billing process for unpaid services, the contents of this file can be used with a report feature on their computer to print invoices for unpaid balance.

As each provider service history/Payment record is updated it can be selected for later batched transmission to the central host. Transmission during the next on-line session is the default, however future record transmission dates can be chosen. Other software operable on the service provider's computer allows the user to select a record in which there are questions, exceptions or other process problems associated and construct a message to the appropriate party (such as the medical insurer/benefit provider, etc) or to request affiliation in a new plan, communication with other service providers or any other party with access to the central host(s).

All communications and updated records are batched for transmission during the next on-line session (or the requested future dated session) with the central host(s).

Software operable on the service provider's computer is used to access the central host(s) and perform security procedures. At that time, files bound for the service provider are transferred from the central host(s) to the service provider's computer and files bound for the central host(s) are transmitted for central host processing.

Figure 8:
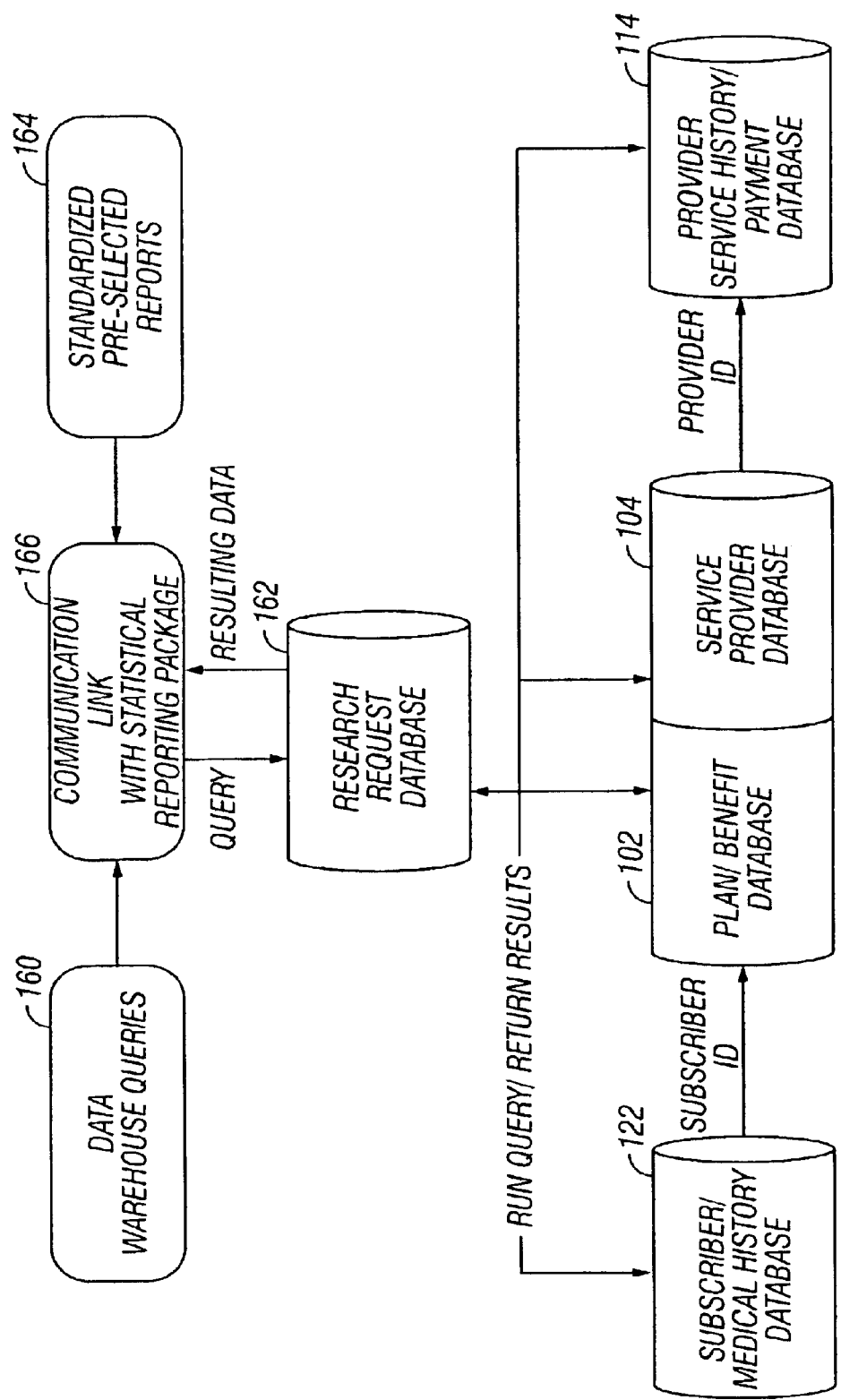
FIG. 8 is a flow diagram of the Medical Research processes according to the preferred embodiment of the invention.

Medical research processes (see FIG. 3, element 60) support research organizations in such areas as product development, public health, utilization and quality review, regulatory and compliance review, education, and scientific and health care research. FIG. 8 is a flow diagram of the medical research processes according to the preferred embodiment of the invention.health care service providers and service recipients can also use the medical research processes to research treatment options and development support and information networks.

Data warehouse queries 160 are conducted using the standardized definitions stored in the data dictionary. The frequency of a data search can be specified. Thus, automated periodic data download subscriptions are available for long-term research projects. Changes may also be made to existing periodic data subscriptions. Using the software operable on the medical researcher's computer, the medical researcher accesses the central host(s), provides required security responses, accesses the Research Request database and downloads data dictionary information for the central host databases (subscriber/medical history 122, Plan/Benefit 102, service provider 104 and provider service history 114) before disconnecting from the central host(s).

This information can be stored on the medical researcher's computer for further data selection, until such time as the information is no longer current (date of last update of the central data dictionary can be checked for currency). The medical researcher can then use software operable on their computer to construct their data query by selecting desired data fields from the data dictionary of the central databases, ensuring from the rules in the data dictionary that appropriate authority is available for access to the data (security rules limit access to certain fields, and requests for non-authorized data will be returned from central host processing with a security restriction message).

Data queries can be specified as one-time only or can be requested on an ongoing, time-specific basis for continuing research efforts. When all data queries have been completed, software within the medical researcher computer accesses the central host(s) and performs the security procedure, then the request file is downloaded to the central host(s) and questions regarding desired implementation dates are answered by the medical researcher.

The change queue request is verified, the medical researcher can disconnect from the central host(s) and the central host(s) performs the data search requests on the appropriate databases and communicates the resulting data extract files (or error messages if the query was not constructed correctly or encountered security restrictions if requests were made for unauthorized information) to the medical researcher for their access and manipulation using software operable on their computer, as needed.

The reporting format for data received in response to such query may also be defined. For example, individual histories can be selected according to such criteria as prognosis, treatment codes, severity of illness, treating organization or individual care unit, and for episodes of care. For confidentiality purposes, data can be stripped of identifying information and searched, for example, by location or diagnostic codes. Information returned from the search can then be accessed by standard data analysis tools or by customized models allowing the researcher to perform the modeling or reporting methods needed to support their project.

A user's query is transmitted to the Research Request database 162 for processing through the Communication Link With Statistical Reporting processes 166. The Research Request database uses the query parameters to link keys within to the appropriate system databases, and the responsive information is returned, for example, electronically (or in print image format, if desired) to the user. This electronic information can then be used for statistical and graphical analysis, for example, by loading into standard statistical software packages.

The health care data can be provided for research, education and monitoring purposes. Such data can be used by health professional schools and programs, accreditation organizations, licensing agencies, disease registries, government agencies, lawyers, health care researchers, clinical investigators, technology developers and manufacturers, health data organizations, health sciences publications, research centers, medical peer review organizations, quality assurance organizations, risk management organizations, utilization review and utilization management organizations, and other users of health care information.

As the researcher is able to define the data elements and parameters of their search, the researcher has significant flexibility in identifying the desired research database, which is selected from the full system databases. Therefore, the data elements and selected values to be extracted can exhibit wide variety and customization to the actual needs of the organization performing the search.

Because of this, the invention can also provides data access for regulatory purposes. Such information includes evidence for litigation, assessment of compliance with laws or standards of care, accreditation of care providers and organizations, and comparisons of health care organizations, professionals and procedures.

For example, if a regulatory agency wished to identify service providers engaged in fraudulent procedures, a search could be constructed defining target codes defining episodes of care from the provider service history/Payment database and, linked to the service provider database, would add identification fields to the targeted records. If insurance plan information were also under investigation and long term analysis of the service recipient care were being analyzed, the search could be extended to select records with linking fields from the Plan/Benefit database and the subscriber/medical history database.

Using the same query selection process this invention permits users to access information for research purposes. Such research purposes include new product development, clinical research, technology assessment, service recipient outcomes, identification of at risk populations, service recipient care effectiveness and treatment cost-effectiveness, and the development of registries and databases.

The invention can also provide data for analysis of past clinical experience within a provider setting. Search parameters of the subscriber/medical history database in these cases would primarily focus on standard diagnostic codes and could return entire case histories for the Researcher's use in modeling and analysis. When analysis of cost-effectiveness are needed, the search parameters would also include information within the provider service history/Payment database. All requested fields for all records would be returned in a relational database format for use by standard relational database modeling systems and applications.

Constructing an appropriate search from all available data dictionary fields, the invention can provide information to assist in policy development, such as resource allocation, workload assessment, risk assessment, strategic planning and public health monitoring, trend analysis, forecast development and cost management. The invention can also provide information for use in the health care industry, such as research and development, marketing strategy planning, case mix documentation, quality assurance planning and implementation, and cost management policy planning and implementation.

Information may be supplied for institutional uses, such as cost reporting, budgetary, productivity and quality assurance purposes, for hospital accreditation, risk management and market placement analysis, personnel recruitment, equipment acquisition, and facilities development.

Standardized pre-selected information processes 164 support integration of new subscription search data with original baseline data for ongoing research. Subscription query criteria or search frequency can be updated and electronically transmitted to the system. For example, adverse reactions to a medication or occurrences of a disease can be automatically tracked over a period of time.

Features of the software operable on the Medical Researcher's computer support simplified processes for appending data returned from ongoing periodic searches of the system databases onto a previously collected relational database located on the medical researcher's computer. The software will provide the data format of the newly retrieved database and will request the target local database. When the researcher identifies the target database, the software will provide the data format of the target database and note any discrepancies. If there are no format discrepancies, the software will perform a record append process. If there are format discrepancies, the software help screens will be available for the researcher to resolve the discrepancies prior to another attempt to append the new data.

The invention also supports comparisons of local, state, national and international health data such as prognosis, treatment options, and cost of care. This information can then be used to promote regional, national and international health objectives. Such information includes data on mortality, morbidity and disability, injuries, personal, environmental and occupational risk factors, preventative and treatment services, costs, and actuarial analyses. As in the descriptions of the data selection process for other disciplines, field values within the databases provide the search base and are performed in the same manner as described above. In this way, service recipient location identifiers, standardized job codes, diagnostic codes for injuries or any other key selection criteria included in the system databases and defined in the data dictionary can be used to provide the researcher with their population base for their chosen research purpose.

Figure 9:
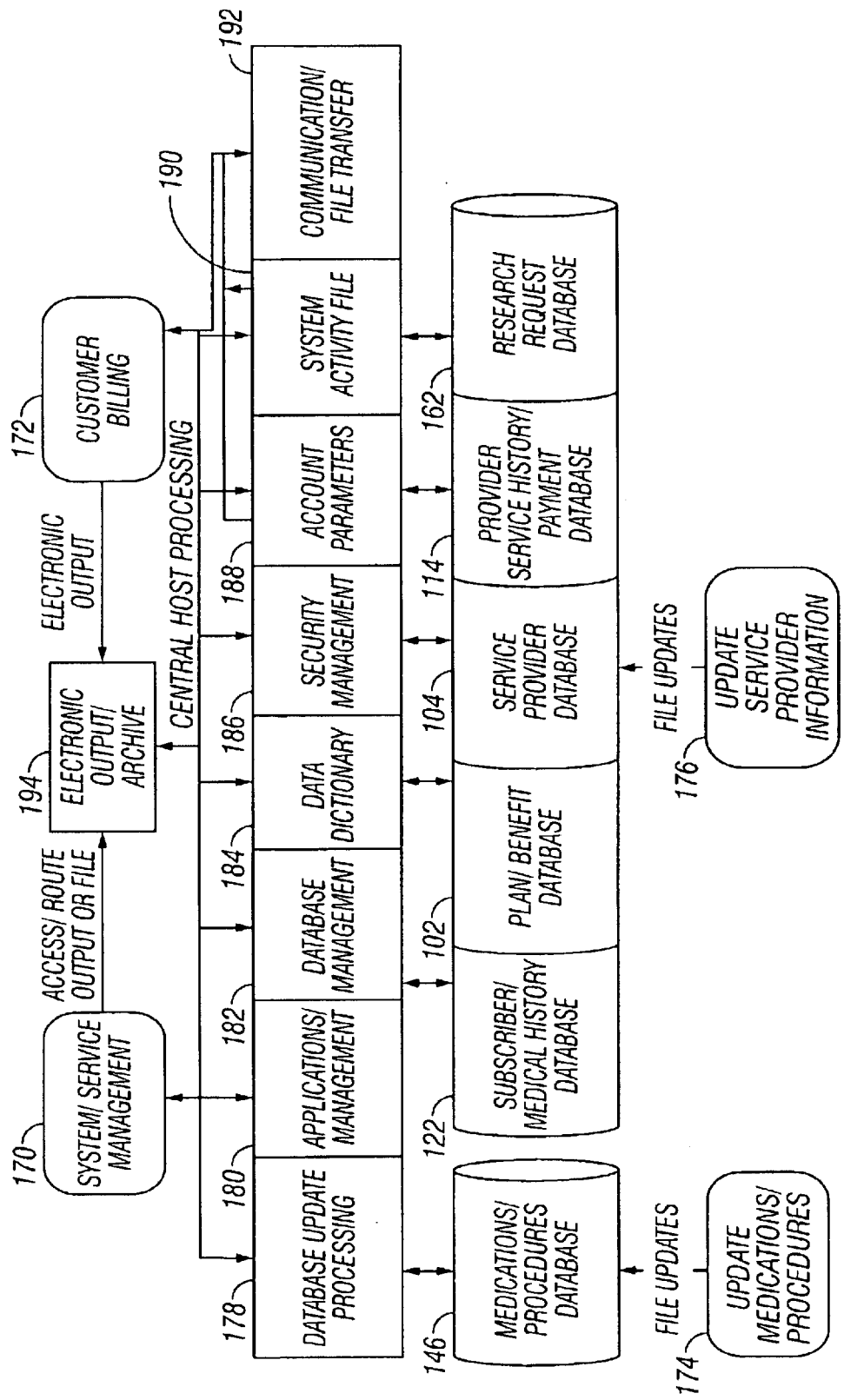
FIG. 9 is a flow diagram of the service support processes, according to the preferred embodiment of the invention.

Service support processes support internal maintenance and product billing functions. FIG. 9 is a flow diagram of the service support (see FIG. 3, element 62) processes, according to the preferred embodiment of the invention. The diagram shows the underlying platform of central host shared processing applications, services and utilities which enable functional use of the central host(s) databases. This shared platform of services includes: database update processing 178, applications/management 180, database management 182, data dictionary 184, security management 186, account parameters 188, system activity file 190, communication/file transfer 192 and a central electronic output/archive 194.

System/service management processes 170 provide system control over processing functionality and service management support for system customers. The shared platform of services are used by all central host computing functions, perform automated processing, update and systems management support functions and are monitored by system maintenance personnel who have override capabilities via central maintenance control panels on their computers.

Among the central host system management functions are full data backup and restore capabilities, for example, ensuring that data stored in the medications/procedures database 146 can be completely restored in the event of a system failure. In this case, a coded instruction set within applications/management 180 would be initiated at a pre-determined time to use a backup utility program under it's central control to perform a backup operation to the electronic output/archive 194. If a database failure were experienced, system maintenance personnel can use their central maintenance control panels on their computers to initiate a restore process on the medications/procedures database.

In the preferred embodiment of the invention, files containing the adjusted values of social security, annuity, retirement account and benefit information are automatically updated. Again, software residing on the local computers of system maintenance personnel can be used to schedule files to be electronically appended to records in the target database. In this case, processing control would be done through database update processing 178 platform functions which would invoke database management 182 services and data dictionary 184 updates if changes to the format of the targeted databases were needed.

Records can be stored on the system indefinitely, or for a specific period of time as defined for each field within each database via retention parameters within the data dictionary. These data dictionary parameters can only be changed through the system maintenance instruction set. Such records can also be archived or purged, if desired, through the data management services which would transmit an archive copy of the database to the electronic output/archive or would invoke purge processing functions within the same shared platform service instruction set.

Security parameters defining access groups and identifying data availability for these groups for each data field (or value range within each field) in each system database are also under secure central host(s) control within the security management 186 platform services. System security staff access computer screens allowing them to define security instruction sets within the security management platform services. These instruction sets provide security access and capability levels for all system users in all system processing activities.

Customer Service features, provides the central setting of account parameters 188 in the central platform services to add new system accounts such as medical insurer/benefit providers, medical researchers and service providers for inclusion in the system, to define billing parties for the system services, any tiered pricing parameters and parent/child account relationships for roll-up billing. In addition, central service control functions are provided via screen entries appended to central host(s) databases. These operate as a central file system override by adding an update record on the target central host(s) database.

This update record is appended to the original record and both the original and the update are maintained to support full audit availability for all system records. In addition, a problem tracking system accessible to all system users can also be implemented under the applications/management 180 set of shared platform services. The preferred embodiment of the invention provides full arbitration and dispute resolution support to all system users by allowing customer service central personnel to use software operable on their computers to scan documents into a database record or select electronic messages, embed them in an electronic folder via the communications/file transfer 192 shared platform services and transmit them to any party with system access.

In support of these dispute resolution capabilities, customer service central personnel have authorized system security access to update any file through appending an attached record to the record under dispute, as described above. In this way a full history on a record is maintained within the central host(s) databases, however a customer service central record can override an automated activity. An example would be a payment dispute, where a service payment was made but has been questioned. As a result of an investigation supporting payment reversal, the customer service central staff member could append a funds reversal record on the provider service history/payment database which would be calculated during the central host(s) service payment accounting cycle as a negative amount during the payment processing cycle and deducted from the value of a future funds transmission between the parties.

Additionally, questions from any system customer regarding system billing can be supported through an on-line billing history archive within the electronic output/archive 194 which allows a customer service central staff member to select the applicable subset of an electronic archived report (in central host administered central storage) created during central host processing cycles and, using software operable on their computer, to embed the contents into an electronic message to the requester, whether that requester is a service provider, a researcher, a medical insurer/benefit provider, a health plan sponsor or a service recipient for transmission by the central host communication feature set within communications/file transfer 192 shared platform services.

The electronic communication features within the messaging/file transfer shared platform services of the invention is available to all central system maintenance, security and customer service staff members to expedite addressing inquiries, problem resolution, setting tiered rates, and making adjustments to rates or for any other customer or system related reason.

Customer billing processes 172 provide integrated service billing for client organizations, such as insurers, sponsors, service providers and research users. As defined in the customer service, support under the System/Service Management functions described above, organizations can define the appropriate billing roll-up in accordance with their individual cost accounting process. These parameters are used during the customer billing processing cycle. During the on-going use by the system users of the system features, as functions are performed counters for the function per account are incremented in the system activity file 190 shared platform services.

On billing processing dates (which can be defined in the Account parameter 188 shared platform facility, the central billing application reads the system activity file and the account parameter records for the billing period and produces an electronic invoice of costs per service categories and total service charges per billing entity. These electronic invoices are transmitted electronically to the customer through the communication/file transfer 192 shared platform service with a copy transmitted to the electronic output/archive 194. If desired, the electronic transmission can accompany an electronic funds transfer from the customer to the system central processing facility, also performed through the Communication/file transfer platform services.

The Update Medications/Procedures 174 processes of the invention provide entry of and changes to standardized codes for all prognoses, treatments, medications and treatments. Designated organizations and agencies can securely add values to field categories within the data dictionary shared platform service and access the medications/procedure database 146 to update medications and procedures information. The authorized agencies can review on-line, download, or print any of the information stored in the medications/procedure database.

Using the software operable on the agency's computer, the user accesses the central host(s), provides required security responses and accesses and downloads the current data dictionary and records within the Medications/procedures database. New information for any of the appropriate sources can be added, deleted or changed manually or through a file append feature within their computer software. Such updates can include the identification via new category codes, descriptions and codes identifying warning conditions or incompatibilities, for new diagnoses, procedures, pharmaceuticals, etc. and can add informational records supporting any of these. Changes are accompanied by active dates, defaulting to current dates, which allow advance notification on developing procedures or for upcoming FDA approval. Batched update features and copy capabilities for current record information is available to simplify changes to records. When all changes have been completed, edited for format correctness and an on-line audit approved, software within the agency's computer accesses the central host(s) and performs the security procedure, then the updated file is downloaded to the central host(s) and questions regarding implementation dates/times, whether and to whom automated notifications are to be generated, and whether other approval communications are needed prior to submitting the change to the data dictionary or the medications/procedures database. The change queue request is verified, the agency can disconnect from the central host(s) and the central host(s) performs the requested operations.

The update service provider information processes 176 are available to permit authorized organizations to create, update and delete information stored in the service provider database 104. This information includes records for licensed practitioners, records for licensed organizations, and organizational ownership information. Service provider records can also be updated to reflect continuing education classes attended by, and disciplinary action taken against a service provider.

Using the software operable on the agency's computer, the user accesses the central host(s), provides required security responses and accesses and downloads the appropriate current records within the service provider database. New licensing, continuing education, disciplinary action, organizational ownership or other information for those records to which the agency has security control can be added, deleted or changed manually or through a file append feature within their computer software.

Changes are accompanied by active dates, defaulting to current dates, which allow advance notification on organizational ownership petitions, for example. Batched update features and copy capabilities for current record information is available to simplify changes to records. When all changes have been completed, edited for format correctness and an on-line audit approved, software within the agency's computer accesses the central host(s) and performs the security procedure, then the updated file is downloaded to the central host(s) and questions regarding implementation dates/times, whether and to whom automated notifications are to be generated, and whether other approval communications are needed prior to submitting the change to the service provider database. The change queue request is verified, the agency can disconnect from the central host(s) and the central host(s) performs the requested operations.

Although the invention is described herein with reference to the preferred embodiment, one skilled in the art will readily appreciate that other applications may be substituted for those set forth herein without departing from the spirit and scope of the present invention.

For example, the functional areas of the invention are extensible to allow secure access to social security, annuity and retirement account and benefit information. Individual service recipients are thereby provided a unified view of their benefit and payment status. This information is accessed using the individual information device. One skilled in the art will readily be able to construct the hardware and software required for the invention using well-known programming techniques and equipment. Accordingly, the invention should only be limited by the claims included below.

What is claimed is:

1. An integrated health care system for collecting, consolidating, conforming, and distributing health care data concerning at least one individual service recipient, the system comprising:

at least one central host computer for maintaining, consolidating, and distributing information generated by any component of said system;
      wherein said centralized host computer is one of a computer, or a network of linked computers having at least one central server;
   at least one provider terminal in communication with said central host computer;
   wherein said provider terminal is one of a portable computer, personal information device, personal digital assistant, personal computer, or server computer;
   at least one portable individual information device for accessing said system;
   wherein said portable individual information device is any of an integrated circuit card, a magnetic storage card, or a portable integrated circuit or microchip-based device;
   a billing module for calculating billing information for a service provided to the at least one individual service recipient;
   an insurance benefits module for calculating available insurance benefits for a service provided to the at least one individual service recipient;
   a payment module for electronically transferring funds to pay a bill for services provided to the at least one individual service recipient, said payment module including at least one shared platform service and at least one database managing processes for billing and payment;
   an authorization module for authorizing service recipient treatment, said authorization module including at least one shared platform service and at least one database managing processes for authorization;
   a messaging module for providing messaging services to a component of said system, said messaging module comprising a communications/file transfer shared platform service that is used for communications between all system participants for all communication features of the system;
   wherein a health care record for said at least one service recipients stored on said central host computer, said provider terminal, and said individual information device;
   wherein said at least one service recipients health care record comprises a structured database of health care records constructed at points of service, an updatable problem list, and care plans, wherein local records are linked to remotely stored records;
   wherein said central host computer, said provider terminal, and said portable individual information device are electronically linked as a network, to permit information distribution to various locations on said network;
   wherein said system is implemented using any of a global communications network, the internet, or a local area network;
   wherein said individual information device stores any of an individual service recipient's insurance information, emergency records, and health care history;
   wherein said provider terminal includes:
      a medical insurer module;
      a health plan sponsor module;
      an individual service recipient module;
      a health care service provider module;
      a health care research module; and
      a service support module;
   wherein said medical insurer module includes functions for plan definition, open enrollment marketing features, automated authorization of benefits, automated referrals, and service payment accounting and;
   wherein said health plan sponsor module includes functions for open enrollment processes, benefit plan information maintenance, and coordination of distribution and activation or deactivation of individual information devices;
   wherein said health care service provider module includes functions for maintaining service recipient records, diagnosing and treating service recipient ailments, managing service payments, accounting services, and maintaining service provider records, including licensing information, staffing affiliations, organizational ownership information, tax identification information, curriculum vitae of licensed practitioners, and well as information regarding disciplinary actions;
   wherein said health care research module includes functions for collecting data on said system for research and analysis of health care issues;
   wherein said service support nodule supports internal maintenance, product billing functions and enablement for module capabilities, said service support module comprising a platform of central host shared processing applications that includes:

database update processing;
applications management;
database management;
a data dictionary;
security management,
a system activity file;
said messaging module; and
central electronic output/archive;
wherein said system provides access to Social Security, annuity, retirement account, and benefit information; and,
wherein said medical insurer module; said health plan sponsor module, said individual service recipient module, said health care service provider module, said health care research module; and said service support module each include databases for storing information; and,
wherein said information is linked and organized by at least one indexing key;
said data dictionary ensuring standardization of all system database elements, wherein said data dictionary includes:
field definitions;
acceptable codes or values organized in acceptable values tables to provide a uniform healthcare vocabulary;
wherein said codes ensure data integrity throughout a data value chain and ensure the data's universal consistency;
edit rules;
format rules;
identification of a field's data owner, wherein the owner has ultimate authority for issuing updates and revisions to the field; and
references to diagnostic, procedural, pharmaceutical and personal information codes for use in processing changes to databases and in construction of research requests to identify potential incompatibilities and problems;
wherein a database accesses data dictionary codes when responding to a query so that information retrieved in response to a query is limited to those cases containing no potential incompatibilities or problems.

2. The system of claim 1, wherein open standards are used for hardware, software, and firmware components of said system.

3. The system of claim 1, wherein said health care research module converts said health care data on said system into one common format for use by said central host computer.

4. The system of claim 3, wherein said health care research module further strips the health care data of any personal information that might compromise the anonymity of the individual service recipient from whom the health care data was collected before distributing the information to any other component of the module.

5. The system of claim 3, further including a statistical analysis module for providing statistical analysis of said common-format health care data stored in said system.

6. The system of claim 5, further comprising a card reader linked to said provider terminal, for accessing information stored on said portable individual information device, and for transmitting information among said portable individual information device and any of said components of said system.

7. The system of claim 6, wherein said provider terminal is operable to communicate with said entire system or any portion of said system, or is operable independently from said system.

8. An integrated health care system, implemented using any of a global communications network, the Internet or a local area network, the system comprising:
at least one central host computer for collecting, conforming, maintaining, consolidating, and distributing information generated by any component of said system;
at least one provider terminal in communication with said central host computer;
wherein said provider terminal is one of a portable computer, personal information device, personal digital assistant, personal computer, or server computer: and,
wherein said provider terminal communicates with said entire system or any portion of said system, or independently from said system;
at least one portable individual information device for accessing said system, wherein said portable individual information device stores an individual service recipients insurance information, emergency records, and health care history;
a card reader, linked to said provider terminal, for accessing information stored on said portable individual information device, and for transmitting information among said portable individual information device and said components of said system;
a messaging module for providing messaging services to said components of said system, said messaging module comprising a communications/file transfer shared platform service that is used for communications between all system participants for all communication features of the system;
wherein a health care record for said service recipient is stored on said central host computer, said provider terminal, and said individual information device;
wherein said at least one service recipient's health care record comprises a structured database of health care records constructed at points of service, an updatable problem list, and care plans, wherein local records are linked to remotely stored records;
wherein said central host computer, said provider terminal, and said portable individual information device are electronically linked as a network, to permit information distribution to various locations on said network;
wherein open standards are used for hardware, software, and firmware components of said system;
wherein said provider terminal includes:
a medical insurer module including functions for plan definition, open enrollment marketing features, automated authorization of benefits, automated referrals, and service payment accounting;
a health plan sponsor module including functions for open enrollment processes, maintenance of benefit plan information, and coordination, distribution, and deactivation of said portable individual information devices;
a health care service provider module including functions for maintaining service recipient records, diagnosing and treating service recipient ailments, service payment management, and accounting services;
a health care research module including functions for the collection of data on said system for research and analysis of health care issues; and, a service support module that supports internal maintenance, product billing functions and enablement for module capabilities, said service support module comprising a platform of central host shared processing applications that includes:
database update processing:
applications management;
database management;
a data dictionary;
security management;
a system activity file;
said messaging module; and
central electronic output/archive;
said data dictionary for ensuring standardization of all system database elements, wherein said data dictionary includes:
field definitions;
acceptable codes or values organized in acceptable values tables to provide a uniform healthcare vocabulary;
wherein said codes ensure data integrity throughout a data value chain and ensure the data's universal consistency;
edit rules;
format rules;
identification of a field's data owner, wherein the owner has ultimate authority for issuing updates and revisions to the field;
references to diagnostic, procedural, pharmaceutical and personal information codes for use in processing changes to databases and in construction of research requests to identity potential incompatibilities and problems;
wherein a database accesses data dictionary codes when responding to a query so that information retrieved in response to a query is limited to those cases containing no potential incompatibilities or problems.

9. The system of claim 8, wherein said health care service provider module further includes
a function for maintenance of service provider records, including licensing information, staffing affiliations, organizational ownership information, tax identification information, curriculum vitae of licensed practitioners, and information regarding disciplinary actions against the health care service provider.

10. The system of claim 9, further comprising an integrated statistical analysis software module for providing statistical analysis of said health care data stored in said system.

11. The system of claim 10, further comprising a billing module for calculating billing information for a service provided to the individual service recipient.

12. The system of claim 11, further comprising an insurance benefits module for calculating available insurance benefits for a service provided to the individual service recipient.

13. The system of claim 9, wherein said centralized host computer is one of a computer, or a network of linked computers having at least one central server.

14. The system of claim 10, further comprising a payment module for electronically transferring funds to pay a bill for services provided to said service recipient, said payment module including at least one shared platform service and at least one database managing processes for billing and payment.

15. The system of claim 10, further comprising an authorization module for authorizing service recipient treatment, said authorization module including at least one shared platform service and at least one database managing processes for authorization.

16. The system of claim 10, wherein said system provides access to any of Social Security, annuity, retirement account, and benefit information, and said statistical analysis module provides comparative statistical analysis of Social Security, retirement account and benefit information.

17. A method for collecting, conforming and consolidating information in an integrated health care system implemented using any of a global communications network, the Internet or a local area network, the method comprising steps of:
maintaining, consolidating, and distributing information generated by a component of said system with at least one central host computer;
providing at least one provider terminal in communication with the central host computer;
wherein said provider terminal is one of a portable computer, personal information device, personal digital assistant, personal computer, or server computer;
wherein the provider terminal is operable to communicate with the entire system or any portion of the system, or is operable independently from the system;
providing at least one portable individual information device for accessing the system, wherein the portable individual information device stores an individual service recipient's insurance information, emergency records, and health care history;
linking a card reader to the provider terminal, for accessing information stored on the portable individual information device, and for transmitting information among the portable individual information device and the components of the system;
providing messaging services to a component of the system;
wherein a health care record for the service recipient is stored on said central host computer, said provider terminal, and said individual information device;
wherein said at least one service recipient's health care record comprises a structured database of health care records constructed at points of service, an updatable problem list, and care plans, wherein local records are linked to remotely stored records;
wherein the central host computer, the provider terminal, and the portable individual information device are electronically linked as a network, to permit information distribution to various locations on said network;
wherein open standards are used for hardware, software, and firmware components of said system; and
providing a data dictionary for ensuring standardization of all system database elements, wherein said data dictionary includes:
field definitions;
acceptable codes or values organized in acceptable values tables to provide a uniform healthcare vocabulary;
wherein said codes ensure data integrity throughout a data value chain and ensure the data's universal consistency;
edit rules;
format rules;
identification of a field's data owner, wherein the owner has ultimate authority for issuing updates and revisions to the field; and references to diagnostic, procedural, pharmaceutical and personal information codes for use in processing changes to databases and in construction of research requests to identify potential incompatibilities and problems;

wherein a database accesses data dictionary codes when responding to a query so that information retrieved in response to a query is limited to those cases containing no potential incompatibilities or problems.

18. The method of claim 17, further comprising steps of:

converting information in the system into a common format for processing by the central host computer;

analyzing the information in the system;

creating resulting analytical data;

converting the resulting analytical data into a format readable by a component of the system; and, distributing the resulting analytical data to a component of the system.

19. The method of claim 18 wherein said analyzing step further includes the step of performing statistical analysis of the information such that resulting analytical data is suitable for use in a clinical research facility;

wherein the clinical research facility is a component of the system; and wherein the clinical research facility further distributes the analytical data to at least one government agency.

20. The method of claim 18 further including a step of stripping the information of any data that might compromise anonymity of the individual from whom the information was collected.

21. The method of claim 17, further comprising steps of:

analyzing information collected by a component of the system;

transmitting resulting analytical data to the central host computer;

converting the resulting analytical data into a common format;

storing the common format analytical data on the central host computer;

converting the common format analytical data into a format usable by any component of the system; and distributing the converted analytical data to any component of the system.

22. The method of claim 21 wherein said analyzing step is performed by a statistical module and wherein the statistical module uses analytical algorithms specific to the component of the system.

* * * * *